US008378172B2

(12) United States Patent
Chye et al.

(10) Patent No.: US 8,378,172 B2
(45) Date of Patent: Feb. 19, 2013

(54) METHODS USING ACYL-COA BINDING PROTEINS TO ENHANCE LOW-TEMPERATURE TOLERANCE IN GENETICALLY MODIFIED PLANTS

(75) Inventors: Mee Len Chye, Hong Kong (CN); Qinfang Chen, Hong Kong (CN); Shi Xiao, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 76 days.

(21) Appl. No.: 12/767,177

(22) Filed: Apr. 26, 2010

(65) Prior Publication Data

US 2010/0333239 A1 Dec. 30, 2010

Related U.S. Application Data

(60) Provisional application No. 61/221,873, filed on Jun. 30, 2009.

(51) Int. Cl.
*C12N 15/82* (2006.01)
(52) U.S. Cl. .................................................. 800/289
(58) Field of Classification Search .................. None
See application file for complete search history.

(56) References Cited

U.S. PATENT DOCUMENTS

| | | | | |
|---|---|---|---|---|
| 7,880,053 B2* | 2/2011 | Chye et al. | ..................... | 800/278 |
| 2004/0216190 A1* | 10/2004 | Kovalic | ......................... | 800/289 |
| 2007/0028333 A1* | 2/2007 | Allen et al. | ..................... | 800/289 |

OTHER PUBLICATIONS

Altschul, S. F. et al. (1990). Basic Local Alignment Search Tool. *Journal of Molecular Biology*, 215:403-410. Academic Press Limited.
Benfey, P. N. et al. (1989). The CaMV 35S enhancer contains at least two domains which can confer different developmental and tissue-specific expression patterns. *The EMBO Journal*, 8(8): 2195-2202. IRL Press.
Browse, J. et al. (1986). Fluxes through the prokaryotic and eukaryotic pathways of lipid synthesis in the "16:3" plant *Arabidopsis thaliana*. *Biochemical Journal*, 235: 25-31.
Chen, Q-F. et al. (2008). Overexpression of the *Arabidopsis* 10-Kilodalton Acyl-Coenzyme A-Binding Protein ACBP6 Enhances Freezing Tolerance[1(O4)]. *Plant Physiology*, 148: 304-315.
Chiang, L. W. et al. (1993). Mutagenic oligonucleotide-directed PCR amplification (mod-PCR): an efficient method for generating random base substitution mutations in a DNA sequence element. *Genome Research*, 2: 210-217. Cold Spring Harbor Laboratory Press.
Chye, M-L et al. (1999). Isolation of a gene encoding *Arabidopsis* membrane-associated acyl-CoA binding protein and immunolocalization of its gene product. *The Plant Journal*, 18(2): 205-214. Blackwell Science Limited.
Chye, M-L et al. (2000). Single amino acid substitutions at the acyl-CoA-binding domain interrupt [14][C]palmitoyl-CoA binding of ACBP2, an *Arabidopsis* acyl-CoA-binding protein with ankyrin repeats. *Plant Molecular Biology*, 44: 711-721. Kluwer Academic Publishers, Netherlands.
Clough, S. J. & Bent, A. F. (1998). Floral dip: a simplified method for Agrobacterium-mediated transformation of *Arabidopsis thaliana*. *The Plant Journal*, 16(6): 735-743. Blackwell Science Ltd.
Coruzzi, G. et al. (1984). Tissue-specific and light-regulated expression of a pea nuclear gene encoding the small subunit of ribulose-1, 5-biphosphate carboxylase. *The Embo Journal*, 3(8): 1671-1679. IRL Press Limited, England.
Elholm, M. et al. (2000). Long-chain acyl-CoA esters and acyl-CoA binding protein are present in the nucleus of rat liver cells. *Journal of Lipid Research*, 41: 538-545.
Engeseth, N. J. et al. (1996). Characterization of an Acyl-CoA-Binding Protein from *Arabidopsis thaliana*. *Archives of Biochemistry and Biophysics*, 331(1): 55-62. Article No. 0282. Academic Press, Inc.
Færgeman, N. J. & Knudsen, J. (1997). Role of long-chain fatty acyl-CoA esters in the regulation of metabolism and in cell signalling. *Biochemistry Journal*, 323: 1-12.
Feddersen, S. et al. (2007). Transcriptional regulation of phospholipid biosynthesis is linked to fatty acid metabolism by an acyl-CoA-binding-protein-dependent mechanism in *Saccharomyces cerevisiae*. *Biochemistry Journal*, 407: 219-230.
Görlich, D. & Mattaj, I. W. (1996). Nucleocytoplasmic Transport. *Science*, 271(5255): 1513-1518. American Association for the Advancement of Science.
Greener, A. et al. (1996). In Vitro Mutagenesis Protocols: Methods in Molecular Biology. vol. 57. Chapter 34: An Efficient Random Mutagenesis Technique Using an *E. coli* Mutator Strain. p. 375.
Helledie, T. et al. (2000). Lipid-binding proteins modulate ligand-dependent trans-activation by peroxisome proliferator-activated receptors and localize to the nucleus as well as the cytoplasm. *Journal of Lipid Research*, 41:1740-1751.
Hills, M. J. et al. (1994). Molecular cloning of a cDNA from *Brassica napus* L. for a homologue of acyl-CoA-binding protein. *Plant Molecular Biology*, 25:917-920. Kluwer Academic Publishers, Belgium.
Horsch, R. B. et al. (1985). A Simple and General Method for Transferring Genes into Plants. *Science*, 227: 1229-1231.
Needleman, S. B. & Wunsch, C. D. (1970). A General Method Applicable to the Search for Similarities in the Amino Acid Sequence of Two Proteins. *Journal of Molecular Biology*, 48: 443-453.
Katagiri, T. et al. (2001). Involvement of a novel *Arabidopsis* phospholipase D, AtPLDδ, in dehydration-inducible accumulation of phosphatidic acid in stress signalling. *The Plant Journal*, 26(6): 595-605. Blackwell Science Ltd.
Kliewer, S. A. et al. (1997). Fatty acids and eicosanoids regulate gene expression through direct interactions with peroxisome proliferator-activated receptors αand γ. *Proceedings of the National Academy of Sciences of the United States of America*, 94(9): 4318-4323. National Academy of Sciences.

(Continued)

*Primary Examiner* — Anne Kubelik
*Assistant Examiner* — Lee A Visone
(74) *Attorney, Agent, or Firm* — Saliwanchik, Lloyd & Eisenschenk

(57) ABSTRACT

ACBP6 can be used to enhance low temperature tolerance in genetically modified plants. An acbp6 T-DNA insertional mutant that lacked ACBP6 mRNA and protein, displayed increased sensitivity to freezing temperature (−8° C.), while ACBP6-overexpressing transgenic *Arabidopsis* were conferred enhanced freezing tolerance. Methods of using ACBP6 to enhance low temperature tolerance of plants are provided.

14 Claims, 17 Drawing Sheets

OTHER PUBLICATIONS

Leung, K-C et al. (2004). ACBP4 and ACBP5, novel *Arabidopsis* acyl-CoA-binding proteins with kelch motifs that bind oleoyl-CoA. *Plant Molecular Biology*, 55: 297-309. Kluwer Academic Publishers, Netherlands.

Li, H-Y & Chye, M-L. (2003). Membrane localization or *Arabidopsis* acyl-CoA binding protein ACBP2. *Plant Molecular Biology*, 51: 483-492. Kluwer Academic Publishers, Netherlands.

Li, W. et al. (2004). The plasma membrane-bound phospholipase Dδ enhances freezing tolerance in *Arabidopsis thaliana*. *Nature Biotechnology*, 22(4): 427-433. Nature Publishing Group.

Li, S. et al. (2006). Systematic Analysis of *Arabidopsis* Organelles and a Protein Localization Database for Facilitating Fluorescent Tagging of Full-Length *Arabidopsis* Proteins. *Plant Physiology*, 141: 527-539.

Li, W. et al. (2008). Differential Degradation of Extraplastidic and Plastidic Lipids during Freezing and Post-freezing Recovery in *Arabidopsis thaliana*. *Journal of Biological Chemistry*, 283(1): 461-468.

Maréchal, É et al. (1997). Lipid synthesis and metabolism in the plastid envelope. *Physiologia Plantarum*, 100:65-77. Denmark.

Mylne, J. & Botella, J. R. (1998). Binary Vectors for Sense and Antisense Expression of *Arabidopsis* ESTs. *Plant Molecular Biology Reporter*, 16: 257-262. Kluwer Academic Publishers, Netherlands.

Nitz, I. et al. (2005). Identification of new acyl-CoA binding protein transcripts in human and mouse. *The International Journal of Biochemistry and Cell Biology*, 37: 2395-2405. Elsevier Ltd.

Ohlrogge, J & Browse, J. (1995). Lipid Biosynthesis. *The Plant Cell*, 7: 957-970. American Society of Plant Physiologists.

Rajashekar, C. B. et al. (2006). Suppression of phospholipase Dα1 induces freezing tolerance in *Arabidopsis*: Response of cold-responsive genes and osmolyte accumulation. *Journal of Plant Physiology*, 163: 916-926. Elsevier GmbH.

Shpaer, E. G. (1996). Sequence Data Analysis Guidebook: Methods in Molecular Biology. vol. 70. Chapter 14: GeneAssist. p. 173.

Sivanandan, C. et al. (2005). T-DNA tagging and characterization of a cryptic root-specific promoter in *Arabidopsis*. *Biochemical et Biophysica Acta*, 1731: 202-208.

Staub, J. M. & Maliga, P. (1994). Translation of psbA mRNA is regulated by light via the 5'-untranslated region in tobacco plastids. *The Plant Journal*, 6(4): 547-553.

Stemmer, W. P. C. (1994). DNA shuffling by random fragmentation and reassembly: In vitro recombination for molecular evolution. *Proceedings of the National Academy of Sciences of the United States of America*, 91(22): 10747-10751. The National Academy of Sciences.

Stemple, D. L. (2004). Tilling—a high-throughput harvest for functional genomics. *Nature Reviews Genetics*, 5: 145-150.

Steponkus, P. L. et al. (1998). Mode of action of the COR15α gene on the freezing tolerance of *Arabidopsis thaliana*. *Proceedings of the National Academy of Sciences of the United States of America*, 95: 14570-14575. The National Academy of Sciences.

Suzui, N. et al. (2006). A putative acyl-CoA-binding protein is a major phloem sap protein in rice (*Oryza sativa* L.). *Journal of Experimental Botany*, 57(11): 2571-2576. Oxford University Press.

Thomashow, M. F. (1999). Plant Cold Acclimation: Freezing Tolerance Genes and Regulatory Mechanisms. *Annual Review of Plant Physiology and Plant Molecular Biology*, 50: 571-599.

Walz, C. et al. (2004). Proteomics of curcurbit phloem exudate reveals a network of defence proteins. *Phytochemistry*, 65: 1795-1804. Elsevier Ltd.

Welti, R. et al. (2002). Profiling Membrane Lipids in Plant Stress Responses. *The Journal of Biological Chemistry*, 277(35): 31994-32002. The American Society for Biochemistry and Molecular Biology, Inc., USA.

Xiao, S. et al. (2008). Overexpression of membrane-associated acyl-CoA-binding protein ACBP1 enhances lead tolerance in *Arabidopsis*. *The Plant Journal*, 54: 141-151. Blackwell Publishing Ltd.

Xiao, S. et al. (2009). Light-regulated *Arabidopsis* ACBP4 and ACBP5 encode cytosolic acyl-CoA-binding proteins that bind phosphatidylcholine and oleoyl-CoA ester. *Plant Physiology and Biochemistry*, 47: 926-933. Elsevier Masson SAS.

Zhang, W. et al. (2004). Phospholipase Dα1-derived phosphatidic acid interacts with ABI1 phosphatase 2C and regulates abscisic acid signaling. *Proceedings of the National Academy of Sciences of the United States of America*, 101(25): 9508-9513. The National Academy of Sciences.

Black, P. N. et al. (2000). Symposium: The Role of the Long Chain Fatty Acyl-CoAs as Signaling Molecules in Cellular Metabolism. Long-Chain Acyl-CoA-Dependent Regulation of Gene Expression in Bacteria, Yeast and Mammals. *The Journal of Nutrition*, 130(2): 305S-309S. American Society for Nutritional Sciences.

Leung, K-C. et al. (2006). *Arabidopsis* ACBP3 is an extracellularly targeted acyl-CoA-binding protein. *Planta*, 223: 871-881.

Mikkelsen, J. & Knudsen, J. (1987). Acyl-CoA-binding protein from cow. *Biochemical Journal*, 248: 709-714.

Petrescu, A. D. et al. (2003). Physical and Functional Interaction of Acyl-CoA-binding Protein with Hepatocyte Nuclear Factor-4α. *The Journal of Biological Chemistry*, 278(51): 51813-51824. The American Society for Biochemistry and Molecular Biology, Inc., USA.

\* cited by examiner

FIG. 8A

**cDNA and gDNA sequences of *ACBP6* (AT1G31812)**

**cDNA sequence of *ACBP6* (625 bp; GenBank accession number NM_102916) (SEQ. ID No: 1)**

```
  1 CCCATATATA TCTCACGCGT TGTCCTCGTC TTCTCCGTCT TACACTGATT
 51 TAATTCTCCT ACCAATCTCA ACTTCCGACG TCTATTCATC ATGGGTTTGA
101 AGGAGGAATT TGAGGAGCAC GCTGAGAAAG TGAATACGCT CACGGAGTTG
151 CCATCCAACG AGGATTTGCT CATTCTCTAC GGACTCTACA AGCAAGCCAA
201 GTTTGGGCCT GTGGACACCA GTCGTCCTGG AATGTTCAGC ATGAAGGAGA
251 GAGCCAAGTG GGATGCTTGG AAGGCTGTTG AAGGGAAATC ATCGGAAGAA
301 GCCATGAATG ACTATATCAC TAAGGTCAAG CAACTCTTGG AAGTTGCTGC
351 TTCCAAGGCT TCAACCTGAT GAATCAAATC CTCATCTGCA GTAACTTTAT
401 CTTAAGCATC AAAATAACAT TGCATAAGAC TTGTTCTTGC TCTTGTGTTT
451 CTATCATATT TAAGCTATCT ACTTTGTGAC ATGGTGTGAT CTCTTAAAAA
501 TGCTTGATAT TGGTTAAAAC AGAGAATCAT GATGCAAACT AAATCCATAA
551 GTTATTTTTG GTCCGTCCTC GATATGGTCT TAGTTAAAAC AGTTGAATTC
601 AAGATGATAT ATTCGTTCTG GTCCG
```

FIG. 8B gDNA sequence of *ACBP6* (1314 bp; GenBank accession number NM_102916) (SEQ. ID No: 2)

```
   1 CCCATATATA TCTCACGCGT TGTCCTCGTC TTCTCCGTCT TACACTGATT
  51 TAATTCTCCT ACCAATCTCA ACTTCCGACG TCTATTCATC ATGGGTTTGA
 101 AGGTACGTTC AGATCCAAAA TGAACCAAAC CGATCTCGGT TTCGGTTTAT
 151 TACTACTCGG ATCTTAGTTT TGTTTGTGTT CACCATTCCT GAATTCTATA
 201 TTTTCTGTGT TGGTAGCCTT GTTTGATCCA GATTTGCAGA TATATAGGTT
 251 CCTTATAGTT ACGAAATTGA AGCTTGTATA GTCAAGAATG ATCACTTTAT
 301 GGAATTGAAT TATTACTGAT CACGCTTTTT CTCTGTATGA TTTTGTCCAT
 351 TTACTGTTCT TATAACTGAT TTGTTAAACA CTGTTTGCTG ATGGGTAATA
 401 TAGTTTTGAA TCTGAGCTAG GTTTGGTTTT ATTGAGTTTT GTTTGATTAT
 451 TGTATCCCGA TTGAGAATTT TAAGTAGTAA TATGTTTGAT GGTGTATTAG
 501 GCTATTAAGA ATCTTTTCTT CGAATTTGTT GTTTCACTGA TTTATATATC
 551 TGCAGGAGGA ATTTGAGGAG CACGCTGAGA AAGTGAATAC GCTCACGGAG
 601 TTGCCATCCA ACGAGGATTT GCTCATTCTC TACGGACTCT ACAAGCAAGC
 651 CAAGTTTGGG CCTGTGGACA CCAGTTAATA TTTTTGTCTG AATATTAACA
 701 TCCTCTATTT TTGCTTCTTA GTTCACTTTT CTGTAATGTT GTTAATAATG
 751 TGTATTTGTT TATTGATTGA TTCAAAGGTC GTCCTGGAAT GTTCAGCATG
 801 AAGGAGAGAG CCAAGTGGGA TGCTTGGAAG GCTGTTGAAG GTACAAAAAC
 851 AATTCAAGTG ATCAACTTTT TTAGCTTAGT GATTTGTTTG TAATTTGGAT
 901 TCTTGTCTCA AGTTCAACAA TTTTTTGTGC TTGGGGAATT GAATTTGAAC
 951 TTTTCTTTGT TTATGATGTC AGGGAAATCA TCGGAAGAAG CCATGAATGA
1001 CTATATCACT AAGGTCAAGC AACTCTTGGA AGTTGCTGCT TCCAAGGCTT
1051 CAACCTGATG AATCAAATCC TCATCTGCAG TAACTTTATC TTAAGCATCA
1101 AAATAACATT GCATAAGACT TGTTCTTGCT CTTGTGTTTC TATCATATTT
1151 AAGCTATCTA CTTTGTGACA TGGTGTGATC TCTTAAAAAT GCTTGATATT
1201 GGTTAAAACA GAGAATCATG ATGCAAACTA AATCCATAAG TTATTTTTGG
1251 TCCGTCCTCG ATATGGTCTT AGTTAAAACA GTTGAATTCA AGATGATATA
1301 TTCGTTCTGG TCCG
```

FIG. 9

Amino acid sequence of ACBP6

The sequences shown here were analyzed by PEPSTATS programme of EMBOSS.

(residues of peptide chosen for raising antibodies are underlined) (SEQ. ID No: 3)

```
 1   MGLKEEFEEH AEKVNTLTEL PSNEDLLILY GLYKQAKFGP VDTSRPGMFS
51   MKERAKWDAW KAVEGKSSEE AMNDYITKVK QLLEVAASKA ST*
```

Molecular weight = 10385.79

FIG. 10A

DNA sequence of (His)$_6$-ACBP6 (SEQ. ID No: 4)

The sequences shown here were analysed by PeptideSort programme of GCG Wilconsin Package Version 10.2.

```
  1    ATGCGGGGTT CTCATCATCAT CATCATCATGG TATGGCTAGCA TGACTGGTGGA
 51    CAGCAAATGG GTCGGGATCTG TACGACGATGA CGATAAGGATC CGAGCTCCACC
101    GCGGTGGCGG CCGCTCTAGAA CTAGTGATTAT ATGGATCCCAC GCGTTGTCCTC
151    GTCTTCTCCG TCTTACACCGA TTTAATTCTCC TACCAATCTCA ACTTCCGACGT
201    CTATTCATCA TGGGTTTGAAG GAGGAATTTGA GGAGCACGCTG AGAAAGTGAAT
251    ACGCTCACGG AGTTGCCATCC AACGAGGATTT GCTCATTCTCT ACGGACTCTAC
301    AAGCAAGCCA AGTTTGGGCCT GTGGACACCAG TCGTCCTGGAA TGTTCAGCATG
351    AAGGAGAGAG CCAAGTGGGAT GCTTGGAAGGC TGTTGAAGGGA AATCATCGGAA
401    GAAGCCATGA ATGACTATATC ACTAAGGTCAA GCAACTCTTGG AAGTTGCTGCT
451    TCCAAGGCTT CAACCTGATGA
```

FIG. 10B

Amino acid sequence of (His)$_6$-ACBP6 (SEQ. ID No: 5)

```
  1    MRGSHHHHHH GMASMTGGQQ MGRDLYDDDD KDPSSTAVAA ALELVIIWIP
 51    RVVLVFSVLH RFNSPTNLNF RRLFIMGLKE EFEEHAEKVN TLTELPSNED
101    LLILYGLYKQ AKFGPVDTSR PGMFSMKERA KWDAWKAVEG KSSEEAMNDY
151    ITKVKQLLEV AASKAST**
```

Number of amino acids: 167      Molecular weight: 18889.5

FIG. 11A

DNA and amino acid sequences of ACBP6::GFP fusion (SEQ. ID No: 6)

Sequences in grey are derived from ACBP6 cDNA and protein. Protein Molecular Weight was calculated by the web-based program The Sequence Manipulation Suite (http://bioinformatics.org/sms/).

DNA sequence of ACBP6::eGFP

```
ATGGGTTTGA AGGAGGAATT TGAGGAGCAC GCTGAGAAAG TGAATACGCT
CACGGAGTTG CCATCCAACG AGGATTTGCT CATTCTCTAC GGACTCTACA
AGCAAGCCAA GTTTGGGCCT GTGGACACCA GTCGTCCTGG AATGTTCAGC
ATGAAGGAGA GAGCCAAGTG GGATGCTTGG AAGGCTGTTG AAGGGAAATC
ATCGGAAGAA GCCATGAATG ACTATATCAC TAAGGTCAAG CAACTCTTGG
AAGTTGCTGC TTCCAAGGCT TCAGGATCCA TGGTGAGCAA GGGCGAGGAG
CTGTTCACCG GGGTGGTGCC CATCCTGGTC GAGCTGGACG GCGACGTAAA
CGGCCACAAG TTCAGCGTGT CCGGCGAGGG CGAGGGCGAT GCCACCTACG
GCAAGCTGAC CCTGAAGTTC ATCTGCACCA CCGGCAAGCT GCCCGTGCCC
TGGCCCACCC TCGTGACCAC CCTGACCTAC GGCGTGCAGT GCTTCAGCCG
CTACCCCGAC CACATGAAGC AGCACGACTT CTTCAAGTCC GCCATGCCCG
AAGGCTACGT CCAGGAGCGC ACCATCTTCT TCAAGGACGA CGGCAACTAC
AAGACCCGCG CCGAGGTGAA GTTCGAGGGC GACACCCTGG TGAACCGCAT
CGAGCTGAAG GGCATCGACT TCAAGGAGGA CGGCAACATC CTGGGGCACA
AGCTGGAGTA CAACTACAAC AGCCACAACG TCTATATCAT GGCCGACAAG
CAGAAGAACG GCATCAAGGT GAACTTCAAG ATCCGCCACA ACATCGAGGA
CGGCAGCGTG CAGCTCGCCG ACCACTACCA GCAGAACACC CCCATCGGCG
ACGGCCCCGT GCTGCTGCCC GACAACCACT ACCTGAGCAC CCAGTCCGCC
CTGAGCAAAG ACCCCAACGA GAAGCGCGAT CACATGGTCC TGCTGGAGTT
CGTGACCGCC GCCGGGATCA CTCTCGGCAT GGACGAGCTG TACAAGCTCG AGTAA
```

FIG. 11B

Amino acid sequence of ACBP6::eGFP (MW: 38.4 kDa) (SEQ. ID No: 7)

| | | | | |
|---|---|---|---|---|
| MGLKEEFEFH | AEKVNTLTEL | PSNEDLLILY | GLYKQAKFGP | VDTSRPGMFS |
| MKERAKWDAW | KAVEGKSSEE | AMNDYITKVK | QLLEVAASKA | SGSMVSKGEE |
| LFTGVVPILV | ELDGDVNGHK | FSVSGEGEGD | ATYGKLTLKF | ICTTGKLPVP |
| WPTLVTTLTY | GVQCFSRYPD | HMKQHDFFKS | AMPEGYVQER | TIFFKDDGNY |
| KTRAEVKFEG | DTLVNRIELK | GIDFKEDGNI | LGHKLEYNYN | SHNVYIMADK |
| QKNGIKVNFK | IRHNIEDGSV | QLADHYQQNT | PIGDGPVLLP | DNHYLSTQSA |
| LSKDPNEKRD | HMVLLEFVTA | AGITLGMDEL | YKLE* | |

SEQUENCE LISTING

```
<160> NUMBER OF SEQ ID NOS: 27

<210> SEQ ID NO 1
<211> LENGTH: 625
<212> TYPE: DNA
<213> ORGANISM: Artificial sequence
<220> FEATURE:
<223> OTHER INFORMATION: Arabidopsis cDNA

<400> SEQUENCE: 1
cccatatata tctcacgcgt tgtcctcgtc ttctccgtct tacactgatt taattctcct      60
accaatctca acttccgacg tctattcatc atgggtttga aggaggaatt tgaggagcac     120
gctgagaaag tgaatacgct cacggagttg ccatccaacg aggatttgct cattctctac     180
ggactctaca agcaagccaa gtttgggcct gtggacacca gtcgtcctgg aatgttcagc     240
atgaaggaga gagccaagtg ggatgcttgg aaggctgttg aagggaaatc atcggaagaa     300
gccatgaatg actatatcac taaggtcaag caactcttgg aagttgctgc ttccaaggct     360
tcaacctgat gaatcaaatc ctcatctgca gtaactttat cttaagcatc aaaataacat     420
tgcataagac ttgttcttgc tcttgtgttt ctatcatatt taagctatct actttgtgac     480
atggtgtgat ctcttaaaaa tgcttgatat tggttaaaac agagaatcat gatgcaaact     540
aaatccataa gttatttttg gtccgtcctc gatatggtct tagttaaaac agttgaattc     600
aagatgatat attcgttctg gtccg                                           625

<210> SEQ ID NO 2
<211> LENGTH: 1314
<212> TYPE: DNA
<213> ORGANISM: Artificial sequence
<220> FEATURE:
```

<223> OTHER INFORMATION: Arabidopsis gDNA

<400> SEQUENCE: 2

```
cccatatata tctcacgcgt tgtcctcgtc ttctccgtct tacactgatt taattctcct      60
accaatctca acttccgacg tctattcatc atgggtttga aggtacgttc agatccaaaa     120
tgaaccaaac cgatctcggt ttcggtttat tactactcgg atcttagttt tgtttgtgtt     180
caccattcct gaattctata ttttctgtgt tggtagcctt gtttgatcca gatttgcaga     240
tatataggtt ccttatagtt acgaaattga agcttgtata gtcaagaatg atcactttat     300
ggaattgaat tattactgat cacgcttttt ctctgtatga ttttgtccat ttactgttct     360
tataactgat ttgttaaaca ctgtttgctg atgggtaata tagttttgaa tctgagctag     420
gtttggtttt attgagtttt gtttgattat tgtatcccga ttgagaattt taagtagtaa     480
tatgtttgat ggtgtattag gctattaaga atcttttctt cgaatttgtt gtttcactga     540
tttatatatc tgcaggagga atttgaggag cacgctgaga aagtgaatac gctcacggag     600
ttgccatcca acgaggattt gctcattctc tacggactct acaagcaagc caagtttggg     660
cctgtggaca ccagttaata ttttttgtctg aatattaaca tcctctattt ttgcttctta     720
gttcactttt ctgtaatgtt gttaataatg tgtatttgtt tattgattga ttcaaaggtc     780
gtcctggaat gttcagcatg aaggagagag ccaagtggga tgcttggaag gctgttgaag     840
gtacaaaaac aattcaagtg atcaactttt ttagcttagt gatttgtttg taatttggat     900
tcttgtctca agttcaacaa ttttttgtgc ttggggaatt gaatttgaac ttttctttgt     960
ttatgatgtc agggaaatca tcggaagaag ccatgaatga ctatatcact aaggtcaagc    1020
aactcttgga agttgctgct tccaaggctt caacctgatg aatcaaatcc tcatctgcag    1080
taactttatc ttaagcatca aaataacatt gcataagact tgttcttgct cttgtgtttc    1140
tatcatattt aagctatcta ctttgtgaca tggtgtgatc tcttaaaaat gcttgatatt    1200
ggttaaaaca gagaatcatg atgcaaacta aatccataag ttattttttgg tccgtcctcg    1260
atatggtctt agttaaaaca gttgaattca agatgatata ttcgttctgg tccg           1314
```

<210> SEQ ID NO 3
<211> LENGTH: 92
<212> TYPE: PRT
<213> ORGANISM: Arabidopsis thaliana

<400> SEQUENCE: 3

```
Met Gly Leu Lys Glu Glu Phe Glu Glu His Ala Glu Lys Val Asn Thr
 1               5                  10                  15

Leu Thr Glu Leu Pro Ser Asn Glu Asp Leu Leu Ile Leu Tyr Gly Leu
                20                  25                  30

Tyr Lys Gln Ala Lys Phe Gly Pro Val Asp Thr Ser Arg Pro Gly Met
            35                  40                  45

Phe Ser Met Lys Glu Arg Ala Lys Trp Asp Ala Trp Lys Ala Val Glu
        50                  55                  60

Gly Lys Ser Ser Glu Glu Ala Met Asn Asp Tyr Ile Thr Lys Val Lys
65                  70                  75                  80

Gln Leu Leu Glu Val Ala Ala Ser Lys Ala Ser Thr
                85                  90
```

<210> SEQ ID NO 4
<211> LENGTH: 507
<212> TYPE: DNA
<213> ORGANISM: Arabidopsis thaliana -continued

<400> SEQUENCE: 4

```
atgcggggtt ctcatcatca tcatcatcat ggtatggcta gcatgactgg tggacagcaa    60
atgggtcggg atctgtacga cgatgacgat aaggatccga gctccaccgc ggtggcggcc   120
gctctagaac tagtgattat atggatccca cgcgttgtcc tcgtcttctc cgtcttacac   180
cgatttaatt ctcctaccaa tctcaacttc cgacgtctat tcatcatggg tttgaaggag   240
gaatttgagg agcacgctga aaagtgaat acgctcacgg agttgccatc caacgaggat   300
ttgctcattc tctacggact ctacaagcaa gccaagtttg gcctgtgga caccagtcgt   360
cctggaatgt tcagcatgaa ggagagagcc aagtgggatg cttggaaggc tgttgaaggg   420
aaatcatcgg aagaagccat gaatgactat atcactaagg tcaagcaact cttggaagtt   480
gctgcttcca aggcttcaac ctgatga                                       507
```

<210> SEQ ID NO 5
<211> LENGTH: 167
<212> TYPE: PRT
<213> ORGANISM: Arabidopsis thaliana

<400> SEQUENCE: 5

```
Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Ser Ser Thr Ala Val Ala Ala Leu Glu Leu Val Ile Ile Trp
        35                  40                  45
Ile Pro Arg Val Val Leu Val Phe Ser Val Leu His Arg Phe Asn Ser
    50                  55                  60
Pro Thr Asn Leu Asn Phe Arg Arg Leu Phe Ile Met Gly Leu Lys Glu
65                  70                  75                  80
Glu Phe Glu Glu His Ala Glu Lys Val Asn Thr Leu Thr Glu Leu Pro
                85                  90                  95
Ser Asn Glu Asp Leu Leu Ile Leu Tyr Gly Leu Tyr Lys Gln Ala Lys
            100                 105                 110
Phe Gly Pro Val Asp Thr Ser Arg Pro Gly Met Phe Ser Met Lys Glu
        115                 120                 125
Arg Ala Lys Trp Asp Ala Trp Lys Ala Val Glu Gly Lys Ser Ser Glu
    130                 135                 140
Glu Ala Met Asn Asp Tyr Ile Thr Lys Val Lys Gln Leu Leu Glu Val
145                 150                 155                 160
Ala Ala Ser Lys Ala Ser Thr
                165
```

<210> SEQ ID NO 6
<211> LENGTH: 1005
<212> TYPE: DNA
<213> ORGANISM: Artificial sequence
<220> FEATURE:
<223> OTHER INFORMATION: Synthetic chimeric construct

<400> SEQUENCE: 6

```
atgggtttga aggaggaatt tgaggagcac gctgagaaag tgaatacgct cacggagttg    60
ccatccaacg aggatttgct cattctctac ggactctaca gcaagccaa gtttgggcct   120
gtggacacca gtcgtcctgg aatgttcagc atgaaggaga gagccaagtg ggatgcttgg   180
aaggctgttg aagggaaatc atcggaagaa gccatgaatg actatatcac taaggtcaag   240
caactcttgg aagttgctgc ttccaaggct tcaggatcca tggtgagcaa gggcgaggag   300
```

```
ctgttcaccg gggtggtgcc catcctggtc gagctggacg gcgacgtaaa cggccacaag      360
ttcagcgtgt ccggcgaggg cgagggcgat gccacctacg gcaagctgac cctgaagttc      420
atctgcacca ccggcaagct gcccgtgccc tggcccaccc tcgtgaccac cctgacctac      480
ggcgtgcagt gcttcagccg ctaccccgac cacatgaagc agcacgactt cttcaagtcc      540
gccatgcccg aaggctacgt ccaggagcgc accatcttct tcaaggacga cggcaactac      600
aagacccgcg ccgaggtgaa gttcgagggc gacaccctgg tgaaccgcat cgagctgaag      660
ggcatcgact tcaaggagga cggcaacatc ctggggcaca agctggagta caactacaac      720
agccacaacg tctatatcat ggccgacaag cagaagaacg gcatcaaggt gaacttcaag      780
atccgccaca acatcgagga cggcagcgtg cagctcgccg accactacca gcagaacacc      840
cccatcggcg acggccccgt gctgctgccc gacaaccact acctgagcac ccagtccgcc      900
ctgagcaaag accccaacga gaagcgcgat cacatggtcc tgctggagtt cgtgaccgcc      960
gccgggatca ctctcggcat ggacgagctg tacaagctcg agtaa                     1005
```

<210> SEQ ID NO 7
<211> LENGTH: 334
<212> TYPE: PRT
<213> ORGANISM: Artificial sequence
<220> FEATURE:
<223> OTHER INFORMATION: Synthetic chimeric construct

<400> SEQUENCE: 7

```
Met Gly Leu Lys Glu Glu Phe Glu Glu His Ala Glu Lys Val Asn Thr
1               5                   10                  15

Leu Thr Glu Leu Pro Ser Asn Glu Asp Leu Leu Ile Leu Tyr Gly Leu
            20                  25                  30

Tyr Lys Gln Ala Lys Phe Gly Pro Val Asp Thr Ser Arg Pro Gly Met
        35                  40                  45

Phe Ser Met Lys Glu Arg Ala Lys Trp Asp Ala Trp Lys Ala Val Glu
    50                  55                  60

Gly Lys Ser Ser Glu Glu Ala Met Asn Asp Tyr Ile Thr Lys Val Lys
65                  70                  75                  80

Gln Leu Leu Glu Val Ala Ala Ser Lys Ala Ser Gly Ser Met Val Ser
                85                  90                  95

Lys Gly Glu Glu Leu Phe Thr Gly Val Val Pro Ile Leu Val Glu Leu
            100                 105                 110

Asp Gly Asp Val Asn Gly His Lys Phe Ser Val Ser Gly Glu Gly Glu
        115                 120                 125

Gly Asp Ala Thr Tyr Gly Lys Leu Thr Leu Lys Phe Ile Cys Thr Thr
    130                 135                 140

Gly Lys Leu Pro Val Pro Trp Pro Thr Leu Val Thr Thr Leu Thr Tyr
145                 150                 155                 160

Gly Val Gln Cys Phe Ser Arg Tyr Pro Asp His Met Lys Gln His Asp
                165                 170                 175

Phe Phe Lys Ser Ala Met Pro Glu Gly Tyr Val Gln Glu Arg Thr Ile
            180                 185                 190

Phe Phe Lys Asp Asp Gly Asn Tyr Lys Thr Arg Ala Glu Val Lys Phe
        195                 200                 205

Glu Gly Asp Thr Leu Val Asn Arg Ile Glu Leu Lys Gly Ile Asp Phe
    210                 215                 220

Lys Glu Asp Gly Asn Ile Leu Gly His Lys Leu Glu Tyr Asn Tyr Asn
225                 230                 235                 240
```

```
Ser His Asn Val Tyr Ile Met Ala Asp Lys Gln Lys Asn Gly Ile Lys
            245                 250                 255

Val Asn Phe Lys Ile Arg His Asn Ile Glu Asp Gly Ser Val Gln Leu
        260                 265                 270

Ala Asp His Tyr Gln Gln Asn Thr Pro Ile Gly Asp Gly Pro Val Leu
    275                 280                 285

Leu Pro Asp Asn His Tyr Leu Ser Thr Gln Ser Ala Leu Ser Lys Asp
290                 295                 300

Pro Asn Glu Lys Arg Asp His Met Val Leu Leu Glu Phe Val Thr Ala
305                 310                 315                 320

Ala Gly Ile Thr Leu Gly Met Asp Glu Leu Tyr Lys Leu Glu
            325                 330

<210> SEQ ID NO 8
<211> LENGTH: 31
<212> TYPE: DNA
<213> ORGANISM: Artificial sequence
<220> FEATURE:
<223> OTHER INFORMATION: Sequence of ACBP6-specific primer ML750

<400> SEQUENCE: 8
atatggatcc cacgcgttgt cctcgtcttc t                                     31

<210> SEQ ID NO 9
<211> LENGTH: 30
<212> TYPE: DNA
<213> ORGANISM: Artificial sequence
<220> FEATURE:
<223> OTHER INFORMATION: Sequence of ACBP6-specific primer ML838

<400> SEQUENCE: 9
caggatcctg aagccttgga agcagcaact                                       30

<210> SEQ ID NO 10
<211> LENGTH: 25
<212> TYPE: DNA
<213> ORGANISM: Artificial sequence
<220> FEATURE:
<223> OTHER INFORMATION: CaMV 35S primer

<400> SEQUENCE: 10
caatcccact atccttcgca agacc                                            25

<210> SEQ ID NO 11
<211> LENGTH: 24
<212> TYPE: DNA
<213> ORGANISM: Artificial sequence
<220> FEATURE:
<223> OTHER INFORMATION: Sequence of ACBP6-specific primer ML751

<400> SEQUENCE: 11
aatatatcat cttgaattca actg                                             24

<210> SEQ ID NO 12
<211> LENGTH: 21
<212> TYPE: DNA
<213> ORGANISM: Artificial sequence
<220> FEATURE:
<223> OTHER INFORMATION: Sequence of COR15a-specific primer ML880

<400> SEQUENCE: 12
gctaacatga gctgttctca c                                                21

<210> SEQ ID NO 13
```

```
<211> LENGTH: 20
<212> TYPE: DNA
<213> ORGANISM: Artificial sequence
<220> FEATURE:
<223> OTHER INFORMATION: Sequence of COR15a-specific primer ML881

<400> SEQUENCE: 13
gaatgtgacg gtgactgtgg                                              20

<210> SEQ ID NO 14
<211> LENGTH: 20
<212> TYPE: DNA
<213> ORGANISM: Artificial sequence
<220> FEATURE:
<223> OTHER INFORMATION: Sequence of COR6.6-specific primer ML882

<400> SEQUENCE: 14
cagagaccaa caagaatgcc                                              20

<210> SEQ ID NO 15
<211> LENGTH: 20
<212> TYPE: DNA
<213> ORGANISM: Artificial sequence
<220> FEATURE:
<223> OTHER INFORMATION: Sequence of COR6.6-specific primer ML883

<400> SEQUENCE: 15
cgtagtacat ctaaagggag                                              20

<210> SEQ ID NO 16
<211> LENGTH: 23
<212> TYPE: DNA
<213> ORGANISM: Artificial sequence
<220> FEATURE:
<223> OTHER INFORMATION: Sequence of COR47-specific primer ML884

<400> SEQUENCE: 16
caagattact ctgctagagg agc                                          23

<210> SEQ ID NO 17
<211> LENGTH: 21
<212> TYPE: DNA
<213> ORGANISM: Artificial sequence
<220> FEATURE:
<223> OTHER INFORMATION: Sequence of COR47-specific primer ML885

<400> SEQUENCE: 17
gtatacgatg agtgttatgg g                                            21

<210> SEQ ID NO 18
<211> LENGTH: 20
<212> TYPE: DNA
<213> ORGANISM: Artificial sequence
<220> FEATURE:
<223> OTHER INFORMATION: Sequence of COR78-specific primer ML886

<400> SEQUENCE: 18
cagaggaacc accactcaac                                              20

<210> SEQ ID NO 19
<211> LENGTH: 20
<212> TYPE: DNA
<213> ORGANISM: Artificial sequence
<220> FEATURE:
<223> OTHER INFORMATION: Sequence of COR78-specific primer ML887

<400> SEQUENCE: 19
```
ctcctctgtt ttctcatctc                                          20

<210> SEQ ID NO 20
<211> LENGTH: 20
<212> TYPE: DNA
<213> ORGANISM: Artificial sequence
<220> FEATURE:
<223> OTHER INFORMATION: Sequence of PLDa1-specific primer ML921

<400> SEQUENCE: 20
tatgcgacga ttgatctgca                                          20

<210> SEQ ID NO 21
<211> LENGTH: 20
<212> TYPE: DNA
<213> ORGANISM: Artificial sequence
<220> FEATURE:
<223> OTHER INFORMATION: Sequence of PLDa1-specific primer ML922

<400> SEQUENCE: 21
ctgagagcct gaatcacatc                                          20

<210> SEQ ID NO 22
<211> LENGTH: 20
<212> TYPE: DNA
<213> ORGANISM: Artificial sequence
<220> FEATURE:
<223> OTHER INFORMATION: Sequence of PLD? -specific primer ML923

<400> SEQUENCE: 22
agcgactcta gctcgaacac                                          20

<210> SEQ ID NO 23
<211> LENGTH: 20
<212> TYPE: DNA
<213> ORGANISM: Artificial sequence
<220> FEATURE:
<223> OTHER INFORMATION: Sequence of PLD? -specific primer ML924

<400> SEQUENCE: 23
caagcataag aagaacccag                                          20

<210> SEQ ID NO 24
<211> LENGTH: 13
<212> TYPE: PRT
<213> ORGANISM: Arabidopsis thaliana

<400> SEQUENCE: 24

Val Glu Gly Lys Ser Ser Glu Glu Ala Met Asn Asp Tyr
1               5                   10

<210> SEQ ID NO 25
<211> LENGTH: 22
<212> TYPE: DNA
<213> ORGANISM: Artificial sequence
<220> FEATURE:
<223> OTHER INFORMATION: Left border primer LBa1

<400> SEQUENCE: 25
tttttcgccc tttgacgttg ga                                       22

<210> SEQ ID NO 26
<211> LENGTH: 21
<212> TYPE: DNA
<213> ORGANISM: Artificial sequence
<220> FEATURE:
<223> OTHER INFORMATION: ACBP6-specific forward primer ML770

```
<400> SEQUENCE: 26
actgatcacg ctttttctct g                                              21

<210> SEQ ID NO 27
<211> LENGTH: 21
<212> TYPE: DNA
<213> ORGANISM: Artificial sequence
<220> FEATURE:
<223> OTHER INFORMATION: ACBP6-specific reverse primer ML771

<400> SEQUENCE: 27
ttctggtata gctcctgcct g                                              21
```

METHODS USING ACYL-COA BINDING PROTEINS TO ENHANCE LOW-TEMPERATURE TOLERANCE IN GENETICALLY MODIFIED PLANTS

CROSS-REFERENCE TO RELATED APPLICATION

The subject application claims the benefit of U.S. Provisional Application Ser. No. 61/221,873, filed Jun. 30, 2009, which is incorporated herein by reference in its entirety, including all figures, tables, amino acid sequences, and nucleic acid sequences.

BACKGROUND

Following de novo fatty acid biosynthesis in the chloroplasts of higher plants (Ohlrogge and Browse, Plant Cell 7: 957-970, 1995), the majority of plastid-synthesized fatty acids are exported as palmitoyl-CoA and oleoyl-CoA to the endoplasmic reticulum (ER) for glycerolipid biosynthesis (Browse et al., Biochem J 235: 25-31, 1986; Maréchal et al., Physiol Plant 100: 65-77, 1997). Although these acyl-CoA derivatives move between the plastids and the ER via the cytosol (Ohlrogge and Browse, Plant Cell 7: 957-970, 1995), proteins that facilitate such transfer have not been identified. A potential candidate is the 10-kD acyl-CoA-binding protein (ACBP) in Arabidopsis thaliana because its derivative has been shown to bind oleoyl-CoA and protect it from degradation by microsomal acyl hydrolases (Engeseth et al., Arch Biochem Biophys 331: 55-62, 1996). To experimentally verify its subcellular localization and biological functions, we carried out further investigations on the 10-kD Arabidopsis ACBP.

In Arabidopsis, a total of six forms of acyl-CoA binding proteins (ACBPs) are present and they include the 10-kD ACBP (Engeseth et al., Arch Biochem Biophys 331: 55-62, 1996) hereby designated as ACBP6 (Xiao et al., Plant J 54: 141-151, 2008), and five other forms ranging from 37.5 to 73.1 kD (Leung et al., Plant Mol Biol 55: 297-309, 2004). Membrane-associated ACBP1 and ACBP2 are subcellularly localized to the ER and plasma membrane (Chye et al., Plant J 18: 205-214, 1999; Li and Chye, Plant Mol Biol 51: 483-492, 2003), ACBP3 is extracellularly-targeted (Leung et al., Planta 223: 871-881, 2006) and kelch-motif-containing ACBP4 and ACBP5 (Leung et al., Plant Mol Biol 55: 297-309, 2004), as well as ACBP6 are localized in the cytosol (Chen et al., Plant Physiol 148: 304-315). Only homologs of ACBP6 have been well-characterized in other eukaryotes (Hills et al., Plant Mol Biol 25: 917-920, 1994; Faergeman and Knudsen, Biochem J 323: 1-12, 1997). Domains that potentially mediate protein-protein interactions, ankyrin repeats (ACBP1 and ACBP2) and kelch motifs (ACBP4 and ACBP5) (Leung et al., Plant Mol Biol 55: 297-309, 2004; Li and Chye, Plant Mol Biol 54: 233-243, 2004), are evident in the larger ACBPs. Using His-tagged recombinant proteins and site-directed mutagenesis, the function of the acyl-CoA-binding domain in binding acyl-CoA esters was established for ACBP1 to ACBP5 (Chye et al., Plant Mol Biol 44: 711-721, 2000; Leung et al., Plant Mol Biol 55: 297-309, 2004; Planta 223: 871-881, 2006). Differential binding to various acyl-CoA esters imply that Arabidopsis ACBPs have various cellular functions.

Mammalian homologs of ACBP6 bind and transport cytosolic acyl-CoA esters and participate in gene regulation by interacting with nuclear factor-4α, a transcriptional activator of genes associated with lipid and glucose metabolism in nuclei of rat hepatocytes (Mikkelsen and Knudsen, Biochem J 248: 709-714, 1987; Black et al., J Nutr 130: 305S-309S, 2000; Elholm et al., J Lipid Res 41: 538-545, 2000; Petrescu et al., J Biol Chem 278: 51813-51824, 2003). The 10-kD bovine ACBP has been identified as a cytosolic protein (Mikkelsen and Knudsen, Biochem J 248: 709-714, 1987) while ACBP6 homologs are localized in the cytoplasm and nuclei of both monkey kidney fibroblast CV-1 cells (Helledie et al., J Lipid Res 41: 1740-1751, 2000) and human hepatocellular liver carcinoma cells (Nitz et al., Int J Biochem Cell Biol 37: 2395-2405, 2005).

ACBP6 homologs have been identified in phloem exudates in cucumber (Cucumis sativus), pumpkin (Cucurbita maxima; Walz et al., Photochemistry 65: 1795-1804, 2004) and rice (Oryza sativa) (Suzui et al., J Exp Bot 57: 2571-2576, 2006), suggesting that plant 10-kD ACBPs may be associated with long-distance transport (possibly of long-chain acyl-CoA esters) and/or in stress and defense since phloem proteins primarily belong to these classes (Walz et al., Photochemistry 65: 1795-1804, 2004; Suzui et al., J Exp Bot 57: 2571-2576, 2006). Our investigations on the response of Arabidopsis ACBP6 to abiotic and biotic stresses further showed that ACBP6 expression is cold (4° C.)-inducible, the acbp6 knockout mutant displays enhanced sensitivity to freezing treatment (−8° C.), and transgenic Arabidopsis overexpressing ACBP6 are conferred freezing-tolerance (Chen et al., Plant Physiol 148: 304-315).

BRIEF SUMMARY OF THE INVENTION

Many tropical and subtropical crops are susceptible to low temperatures (chilling and freezing). Examples of cold-susceptible crops include citrus (orange, grapefruit), rice, tomato, grapevine, banana, peach, nectarines, carambola, eggplant, papaya, peppers, zucchini, squash, mung bean, mango, and cotton.

Enhancing their tolerance can result in protection at germination, flowering (many blooms are temperature-sensitive), fruit development, or even storage post-harvest. We can express ACBP6 in crop plants to help them withstand freezing temperatures and extend cultivation zones, for growing flowers, fruits, vegetables and other crops. Freezing and chilling in low/freezing temperatures are routine methods to extend storage and shelf-life of such plants and their products.

An aspect of the present invention is based on the observation that genetically modified plants and progeny thereof expressing acyl-CoA-binding proteins, exemplified herein by the Arabidopsis ACBP6 protein, can be provided with improved low-temperature tolerance as compared to non-modified plants. Presented herein are plant transformation vectors wherein each comprises a nucleic acid sequence encoding an ACBP6 that can be used to generate genetically-transformed plants via nuclear transformation or plastid transformation. The resultant plants that overexpress ACBP6, exemplified herein by Arabidopsis ACBP6, are conferred the ability to tolerate lower temperatures than wild-type plants.

In accordance with another aspect of the present invention, there are provided plant transformation vectors (including both nuclear and plastid transformation vectors) comprising polynucleotides which encode Arabidopsis ACBP6 or functional variants of ACBP6 polypeptides. In specific embodiments, the invention provides for transformed plants such as transgenic or transplastomic Arabidopsis, tomato, tobacco, cotton, and rice plants. The present invention provides modified plants that comprise ACBP6 polypeptides or variants thereof able to convey to the host organism similar low-temperature tolerance as the ACBP6 polypeptides. The present invention also provides a method of producing the modified plants which comprises transforming a plant with a plastid and/or nuclear transformation vector comprising at least one ACBP6-encoding polynucleotide.

Plant cells containing a vector comprising a polynucleotide encoding a polypeptide exhibiting ACBP6 activity are also an aspect of this invention. Plant parts of the modified plants, such as for example, fruits, leaves, tubers, seeds, flowers, stems or roots, which comprise cells expressing ACBP6 polypeptides are provided in the invention. The plant parts include parts that are separated from the whole plant or attached onto the whole plant.

In a specific embodiment, a nuclear transformation vector is used to cause expression of one or more ACBP6s including *Arabidopsis* ACBP6 polypeptides or variants thereof conveying similar low-temperature tolerance as the *Arabidopsis* ACBP6 polypeptides. In a specific embodiment, a plastid transformation vector is used to cause expression of one or more ACBP6s including *Arabidopsis* ACBP6 polypeptides or variants thereof conveying similar low-temperature tolerance as the *Arabidopsis* ACBP6 polypeptides. Such nuclear and plastid transformation vectors can be used alone or in conjunction with each other or with other recombinant vectors that can enhance the low-temperature tolerance of plants transformed therewith.

The present invention provides a method of producing ACBP6 polypeptides in plants. The method comprises transforming a plant with a vector which comprises a polynucleotide coding for one or more ACBP6 polypeptides. The vector can optionally also comprise a promoter, operably linked to the coding sequence, and a terminator, and/or other regulatory elements. The vector can be designed to introduce the heterologous polypeptide so that it will be expressed under the control of a plant's own endogenous promoter, such as, for example, in the pseudogene technique taught by Hahn and Kuehnle (US 2003-003362641), and incorporated herein by reference. Alternatively, or in addition, the vector can contain a constitutive and/or inducible and/or tissue specific promoter operatively linked to the ACBP6-encoding polynucleotide. Plant cells containing a vector which comprises one or more nucleic acid sequences encoding ACBP6 are also an aspect of this invention. Alternatively, the plant cells may contain one or more ACBP6 vectors. Each vector may contain an exogenous polynucleotide encoding one polypeptide exhibiting the low-temperature tolerance activity of an ACBP6, or optionally may contain an operon encoding more than one such ACBP6 polypeptide. The present invention provides plant parts, such as for example, fruits, leaves, tubers, seeds, flowers, stems, roots, and all other anatomical parts of the modified plant.

The present invention also provides a method of obtaining enhanced low-temperature tolerance in a plant cell comprising: obtaining a plant cell genetically modified to express ACBP6; and exposing the plant cell to temperatures low enough to be growth-inhibiting to a native plant cell of the same type.

The present invention also provides a method of obtaining a plant part having low-temperature tolerance, comprising: obtaining a plant part genetically modified to express ACBP6; and growing the plant part under conditions where it is exposed to frost or freeze.

The present invention also provides a method of screening for functional ACBP6 variants, comprising: obtaining a cell genetically modified to express a candidate ACBP6 variant; growing the cell under conditions wherein the temperature of the cell's environment is lowered to an extent and for a duration that is sufficient to be growth-inhibiting to a native cell of the same type; observing whether the cell exhibits a reduction in growth inhibition; and, if so, identifying the candidate ACBP6 variant as functional.

DESCRIPTION OF THE DRAWINGS

FIG. 1 *Arabidopsis* ACBP6 is localized in the cytosol.
A, Northern blot analysis with digoxygenin-labelled ACBP6 cDNA of five independent 35S::ACBP6-GFP transgenic lines (lanes 1-5). Arrow, ACBP6-GFP mRNA. Arrowhead, ACBP6 mRNA. RNA gel (30 µg/lane) stained with ethidium bromide at bottom. WT, wild type.
B, Western blot analyses using anti-GFP (top) and ACBP6-specific (bottom) antibodies on the same five independent 35S::ACBP6-GFP lines. ACBP6-GFP (arrow) and GFP (arrowhead) cross-reacting bands are indicated. Bottom, identically loaded gel stained with Coomassie Blue. WT, wild type; V, vector-transformed control.
C, Confocal microscopy of premature root cells of *Arabidopsis* 35S::ACBP6-GFP line 1 (top) showing localization of ACBP6-GFP in the cytosol (arrows) and nuclei (arrowheads). Bottom, GFP vector transformed *Arabidopsis*. Bars=20 µm.
D, Western blot analysis using anti-GFP antibodies on subcellular fractions of whole-plant protein from transgenic *Arabidopsis* 35S::ACBP6-GFP line 1. Subcellular fractions from total whole-plant protein (lane 1), membrane (lane 2), cytosol (lane 3), large particles including mitochondria, chloroplasts and peroxisomes (lane 4), and nuclei (lane 5). Arrowhead, 38.4-kD ACBP6-GFP cross-reacting band. Bottom, identically loaded gel stained with Coomassie Blue.
E, Western blot analysis using ACBP6-specific antibodies on subcellular fractions of whole plant protein from wild-type *Arabidopsis*. Subcellular fractions from total whole-plant protein (lane 1), membrane (lane 2), cytosol (lane 3), large particles including mitochondria, chloroplasts and peroxisomes (lane 4), and nuclei (lane 5). Arrow, 10.4-kD ACBP6 cross-reacting band. Bottom, identically loaded gel stained with Coomassie Blue.

FIG. 2 Expression of ACBP6 mRNA and protein in wild-type *Arabidopsis*.
A, Spatial expression of ACBP6 in various tissues (L, leaf; R, root; St, stalk; Si, silique; F, flower) by northern blot analysis using a digoxygenin-labelled probe prepared from full-length ACBP6 cDNA. Total RNA (30 µg/well) hybridized to ACBP6 cDNA. Bottom, ethidium bromide-stained gel before blotting.
B, Western blot analysis using ACBP6-specific antibodies (top). Bottom, identically loaded gel stained with Coomassie Blue.
C, Northern blot shows cold-induction of ACBP6 expression. Total RNA isolated from rosettes of wild-type *Arabidopsis* at the indicated times after treatment (hours after treatment [hpt]) at 4° C. indicates. Bottom, RNA gel (30 mg/lane) stained with ethidium bromide.
D, Western blot using ACBP6-specific antibodies on total protein extracted from cold-treated rosettes from wild-type *Arabidopsis* (top). Bottom, identically loaded gel stained with Coomassie Blue.

FIG. 3 Characterization of an acbp6 knockout mutant (SALK_104339) and 35S::ACBP6 transgenic *Arabidopsis* lines.

Figure 1A:
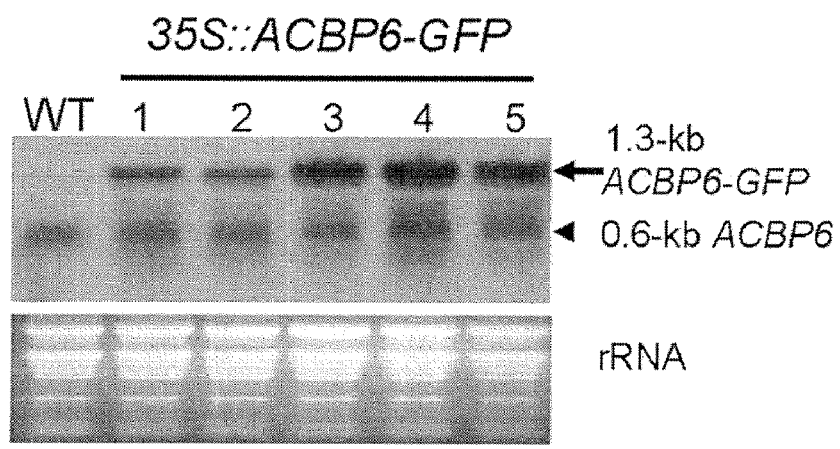
FIGS. 1-7 and related description in the text have been reproduced from Chen et al 2008; Plant Physiology 148: 304-315 (www.plantphysiol.org; copyright American Society of Plant Biologists)

A, T-DNA insertion in the third intron of ACBP6 resulted in a 37-bp deletion (boldface in the wild type [WT] sequence). Locations of primers used for genotyping the acbp6 allele are indicated.

B, Specificity of the primer combinations, ML770 and ML771 (top gel) and LBa1 and ML771 (bottom gel) in PCR to identify acbp6 homozygous mutants (lanes 3 and 4). Lanes 2 and 5 resemble wild type (WT) samples. Lane 1, heterozygous mutant.

C, Northern blot analysis on wild type (WT), acbp6 mutant and ACBP6 overexpressors (OE-3, OE-5 and OE-7) using a digoxygenin-labelled ACBP6 cDNA probe. The acbp6 homozygous mutant lacked ACBP6 mRNA. ACBP6-OE lines show higher ACBP6 expression than wild type. Total RNA (30 µg/lane) stained with ethidium bromide before blotting is shown at bottom.

D, Western blot analysis using ACBP6-specific antibodies. Total protein (15 µg/lane) extracted from rosettes of wild type (WT), acbp6 mutant and three independent ACBP6-overexpressors (OE-3, OE-5 and OE-7). Bottom, identically loaded gel stained with Coomassie Blue.

FIG. 4 ACBP6-overexpressors are freezing tolerant.
A, Testing of freezing tolerance using ACBP6-overexpressor (OE-3) lines at different temperatures below freezing. NA and CA wild-type (WT), acbp6 mutant and ACBP6-overexpressor (OE-3) plants were photographed after 7-d recovery at 16 h light (23° C.)/8 h dark (21° C.) cycles. A similar phenotype was observed with another ACBP6-overexpressor line tested (OE-5; data not shown).
B, Electrolyte leakage of NA and CA wild type (WT), acbp6 mutant and ACBP6-overexpressors (OE-3) after 1 h treatment at temperatures below freezing, followed by thawing at 4° C. overnight. For cold-acclimation (CA), plants were incubated at 4° C. for 3 d. Nonacclimated (NA) plants remained in a growth chamber at 23° C. until measurements. Asterisk indicates significant difference from wild type ($P<0.05$). Values are means±SD (n=3) calculated from three independent experiments.
C, Phenotypes of NA and CA 11-day-old wild type (WT), acbp6 mutant and ACBP6-overexpressors (OE-3 and OE-5) seedlings after freezing treating at −12° C. for 1 h. Plates were thawed overnight at 4° C. and transferred to a growth chamber (16 h light [21° C.]/8 h dark [21° C.] photoperiods) for a 7-d recovery before photography.
D, Survival rate of NA and CA wild-type (WT), acbp6 mutant and ACBP6-overexpressors (OE-3 and OE-5) seedlings after freezing treatment at −12° C. for 1 h, followed by growth at 23° C. for 7 d. Asterisk indicates significant difference from wild type (double asterisk, $P<0.01$; single asterisk, $P<0.05$). Values are means±SD (n=3) calculated from three independent experiments.

FIG. 5 Northern blot analysis of COR, PLDα1 and PLDδ expression in wild type (WT), acbp6 mutant and ACBP6-overexpressor (OE-3 and OE-5) plants.
A, COR47, COR6.6, COR78 and COR15a expression using digoxygenin-labelled PCR-generated cDNA probes. The membrane was subsequently stripped and hybridized to digoxygenin-labelled ACBP6 cDNA probe. Total RNA were extracted from rosettes of wild-type, acbp6, and transgenic Arabidopsis before (NA) and after (CA) cold acclimation for 3 d. Bottom, total RNA (30 µg/lane) stained with ethidium bromide.
B, PLDα1 and PLDδ expression in wild type (WT), acbp6 mutant and ACBP6-overexpressor (OE-3 and OE-5) plants. Total RNA (30 µg/lane) extracted from rosettes of WT, acbp6, OE-3 and OE-5 harvested before acclimation (NA) or after (CA) 3-d cold acclimation, followed by freezing at −8° C. for 1 h (F), and thawing at 4° C. for 8 h (T).

Figure 6:
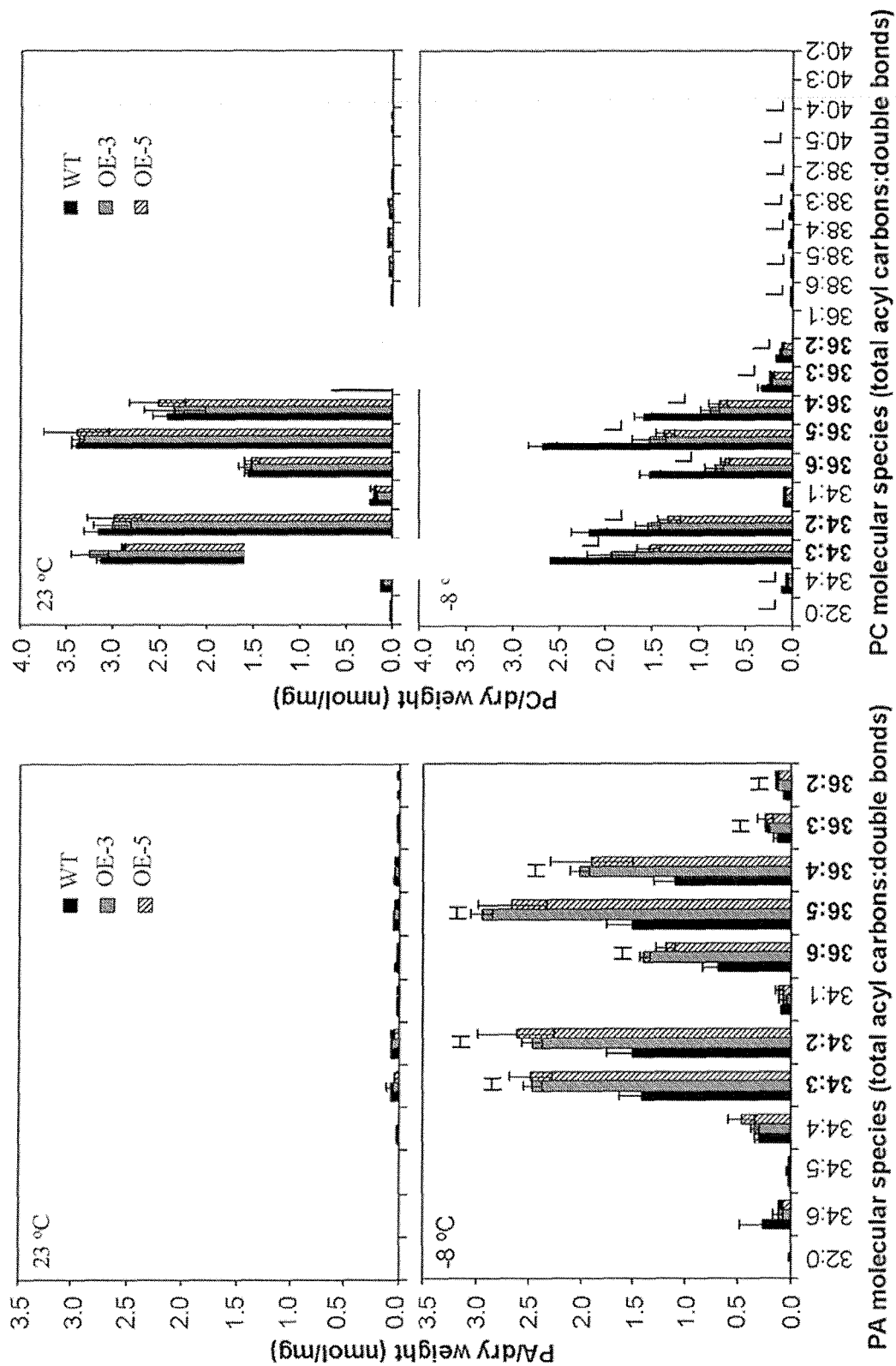

FIG. 6 Freezing-induced changes in PA and PC species of Arabidopsis wild type (WT) and ACBP6-overexpressors (OE-3 and OE-5) before and after CA followed by freezing treatment. The black bar represents WT and the hatched bars represent OE-3 and OE-5, respectively. Numbers in boldface indicate the species with increases in PA that have corresponding decreases in PC. H, value higher than the WT ($P<0.05$); L, value lower than the WT ($P<0.05$). Values are the means±SD (n=3).

Figure 7A:
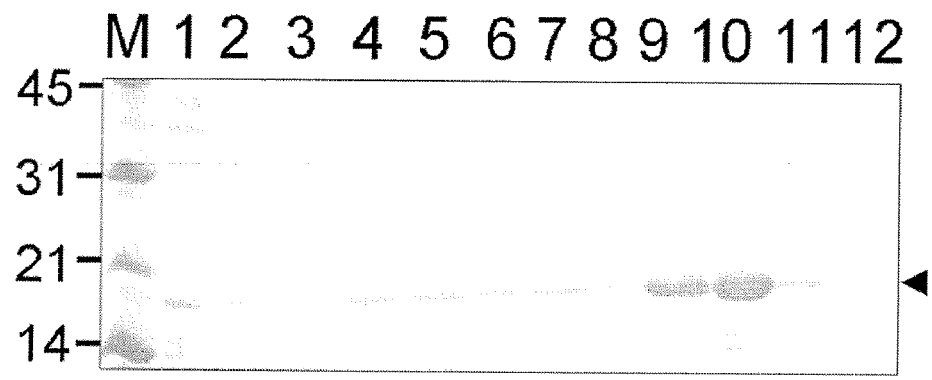

FIG. 7 Purification of $(His)_6$-ACBP6 recombinant protein and its interaction with PC.
A, Purification of $(His)_6$-ACBP6 recombinant protein. An SDS-PAGE gel shows the 18.9-kD $(His)_6$-ACBP6 protein purified from E. coli at 3 h after isopropylthio-β-galactoside induction. M, marker; lane 1, flow through fraction; lane 2, washing fraction at pH 6.3; lanes 3-8, eluted fractions at pH 5.9; lanes 9-12, eluted fractions at pH 4.5.
B, $(His)_6$-ACBP6/lipid binding on filters. Various concentrations (0, 12.5, 25.0 and 32.5 µM) of lipids (PA, PC and LysoPC) were spotted onto nitrocellulose and incubated with 1 µg/ml of purified $(His)_6$-ACBP6 protein. The $(His)_6$-ACBP6/lipid binding was detected by immunoblotting with HRP-conjugated anti-penta-His antibodies.
C, Effect of PC acyl species on $(His)_6$-ACBP6/lipid binding. Fifty µM lipid (PC, 16:0-PC, 18:0-PC, 18:1-PC, 18:2-PC or DMPC) spotted onto nitrocellulose was incubated with 1 µg/ml of purified $(His)_6$-ACBP6 protein. The $(His)_6$-ACBP6/lipid binding was detected by immunoblotting with HRP-conjugated anti-penta-His antibodies.

FIGS. 8A-B depict the cDNA and gDNA sequences, respectively, of ACBP6 (AT1G31812).

FIG. 9 depicts the amino acid sequence of ACBP6. The sequence shown here was analyzed by PEPSTATS programme of EMBOSS. Residues of the ACBP6 peptide chosen for raising antibodies are underlined.

FIGS. 10A-B depict the DNA and amino acid sequences, respectively, of $(His)_6$-ACBP6.

FIGS. 11A-B depict the DNA and amino acid sequences, respectively, of ACBP6::GFP fusion.

Figure 12:
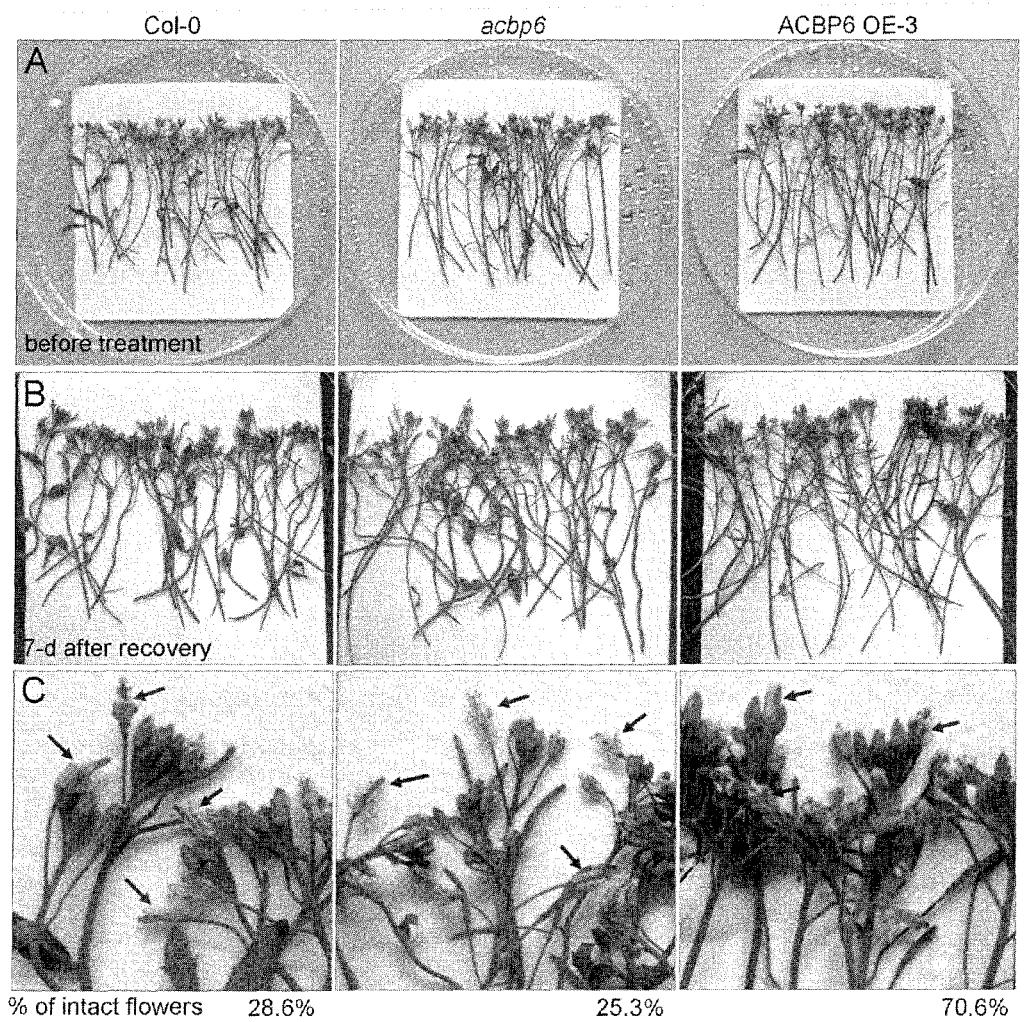

FIGS. 12A-C Freezing treatment of flowers detached from 6-week-old wild type, acbp6 and ACBP6 OE-3 plants.
A, CA-treated flowers detached from 6-week-old wild type (WT), acbp6 mutant and ACBP6-overexpressors (OE-3) plants.
B, Images of the CA flowers in (A) after freezing treating at −5° C. for 1 h. Flowers were then subject to a 7-d recovery at 4° C. for before photography.
C, Close-up images of flowers in (B). Numbers at the bottom show the percentage of intact flowers in (B).

BRIEF DESCRIPTION OF THE SEQUENCES

SEQ ID NO:1 cDNA sequence of ACBP6
SEQ ID NO:2 gDNA sequence of ACBP6
SEQ ID NO:3 Amino acid sequence of ACBP6
SEQ ID NO:4 DNA sequence of $(His)_6$-ACBP6
SEQ ID NO:5 Amino acid sequence of $(His)_6$-ACBP6
SEQ ID NO:6 DNA sequence of ACBP6::GFP fusion
SEQ ID NO:7 Amino acid sequence of ACBP6::eGFP
SEQ ID NO:8 Sequence of ACBP6-specific primer ML750
SEQ ID NO:9 Sequence of ACBP6-specific primer ML838
SEQ ID NO:10 Sequence of CaMV 35S promoter-specific forward primer 35SB
SEQ ID NO:11 Sequence of ACBP6-specific primer ML751
SEQ ID NO:12 Sequence of COR15a-specific primer ML880

SEQ ID NO:13 Sequence of COR15a-specific primer ML881
SEQ ID NO:14 Sequence of COR6.6-specific primer ML882
SEQ ID NO:15 Sequence of COR6.6-specific primer ML883
SEQ ID NO:16 Sequence of COR47-specific primer ML884
SEQ ID NO:17 Sequence of COR47-specific primer ML885
SEQ ID NO:18 Sequence of COR78-specific primer ML886
SEQ ID NO:19 Sequence of COR78-specific primer ML887
SEQ ID NO:20 Sequence of PLDα1-specific primer ML921
SEQ ID NO:21 Sequence of PLDα1-specific primer ML922
SEQ ID NO:22 Sequence of PLDδ-specific primer ML923
SEQ ID NO:23 Sequence of PLDδ-specific primer ML924
SEQ ID NO:24 Synthetic peptide corresponding to amino acids 63 to 75 of ACBP6
SEQ ID NO:25 T-DNA left border primer LBa1
SEQ ID NO:26 ACBP6-specific forward primer ML770
SEQ ID NO:27 ACBP6-specific reverse primer ML771

DETAILED DESCRIPTION

As used herein, the term "modified plant or plant parts" refers to a plant or plant part, whether it is attached or detached from the whole plant. It also includes progeny of the modified plant or plant parts that are produced through sexual or asexual reproduction.

"Progeny" includes the immediate and all subsequent generations of offspring traceable to a parent.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" or "native" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring, and includes "wild-type" plants.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in is "endogenous to") a given host microorganism or host cell (e.g., the nucleic acid comprises a nucleotide sequence endogenous to the host microorganism or host cell); however, in the context of a heterologous nucleic acid, the same nucleotide sequence as found endogenously is produced in an unnatural (e.g., greater than expected or greater than naturally found) amount in the cell, or a nucleic acid comprising a nucleotide sequence that differs in sequence from the endogenous nucleotide sequence but encodes the same protein (having the same or substantially the same amino acid sequence) as found endogenously is produced in an unnatural (e.g., greater than expected or greater than naturally found) amount in the cell; (c) the nucleic acid comprises two or more nucleotide sequences that are not found in the same relationship to each other in nature, e.g., the nucleic acid is recombinant. An example of a heterologous nucleic acid is a nucleotide sequence encoding an ACBP6 operably linked to a transcriptional control element (for example, a promoter) to which an endogenous (naturally-occurring) ACBP6 coding sequence is not normally operably linked. Another example of a heterologous nucleic acid is a high copy number plasmid comprising a nucleotide sequence encoding an ACBP6. Another example of a heterologous nucleic acid is a nucleic acid encoding an ACBP6, where a host cell that does not normally produce ACBP6 is genetically modified with the nucleic acid encoding ACBP6; because ACBP6-encoding nucleic acids are not naturally found in the host cell, the nucleic acid is heterologous to the genetically modified host cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, for example, the term "recombinant" polynucleotide or nucleic acid refers to one which is not naturally occurring, for example, is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "exogenous nucleic acid" refers to a nucleic acid that is not normally or naturally found in and/or produced by a given bacterium, organism, or cell in nature.

As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The terms "transformation" or "transformed" are used interchangeably herein with "genetic modification" or "genetically modified" and refer to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell or into a plastome of the cell. In prokaryotic cells, permanent changes can be introduced into the chromosome or via extrachromosomal elements such as plasmids, plastids, and expression vectors, which may contain one or more selectable markers to aid in their maintenance in the recombinant host cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (for example, a cell line) cultured as a unicellular entity, which eukaryotic or prokaryotic cells can be, or have been, used as recipients for a nucleic acid (for example, an expression vector that comprises a nucleotide sequence encoding one or more gene products such as ACBPs), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (for example, a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, for example, an exogenous nucleic acid that is foreign to the eukaryotic host cell, or a recombinant nucleic acid that is not normally found in the eukaryotic host cell.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

Expression cassettes may be prepared comprising a transcription initiation or transcriptional control region(s) (for example, a promoter), the coding region for the protein of interest, and a transcriptional termination region. Transcriptional control regions include those that provide for overexpression of the protein of interest in the genetically modified host cell; those that provide for inducible expression, such that when an inducing agent is added to the culture medium, transcription of the coding region of the protein of interest is induced or increased to a higher level than prior to induction.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein; and Sambrook, J. and Russell, W., *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1× SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50 9.51). For hybridizations with shorter nucleic acids, i.e., oligonucleotides, the position of mismatches becomes more important, and the length of the oligonucleotide determines its specificity (see Sambrook et al., supra, 11.7 11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine. An ACBP6 protein containing conserved amino acid substitutions as compared to the *Arabidopsis* ACBP6 protein exemplified herein would fall within the scope of "variants" of *Arabidopsis* ACBP6.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available. Fragments of full-length proteins can be produced by techniques well known in the art, such as by creating synthetic nucleic acids encoding the desired portions; or by use of Bal 31 exonuclease to generate fragments of a longer nucleic acid.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-410. Another alignment algorithm is FASTA, available in the Genetics Computing Group (GCG) package, from Madison, Wis., USA, a wholly owned subsidiary of Oxford Molecular Group, Inc. Other techniques for alignment are described in *Methods in Enzymology*, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the term "variant" refers either to a naturally occurring genetic mutant of ACBP6 or a recombinantly prepared variation of ACBP6, each of which contain one or more mutations in its DNA. The term "variant" may also refer to either a naturally occurring variation of a given peptide or a recombinantly prepared variation of a given peptide or protein in which one or more amino acid residues have been modified by amino acid substitution, addition, or deletion. Preferably, the variants include less than 25, less than 20, less than 15, less than 10, less than 5, less than 4, less than 3, or less than 2 amino acid substitutions, rearrangements, insertions, and/or deletions relative to *Arabidopsis* ACBP6. In this regard, the term "variant" can encompass fragments, derivatives, and homologs of *Arabidopsis* ACBP6.

References to "ACBP6" herein mean *Arabidopsis* ACBP6 and functional variants of *Arabidopsis* ACBP6 (polynucleotides or polypeptides, as indicated by the context) that can convey improved low-temperature tolerance to the host in which they are expressed.

To generate a subject genetically modified host cell according to the subject invention, one or more nucleic acids comprising nucleotide sequences encoding one or more ACBP6 polypeptides that convey low-temperature tolerance is introduced stably or transiently into a parent host cell, using established techniques, including, but not limited to, electroporation, calcium phosphate precipitation, DEAE-dextran mediated transfection, liposome-mediated transfection, particle bombardment, *Agrobacterium*-mediated transformation, and the like. For stable transformation, a nucleic acid will generally further include a selectable marker, for example, any of several well-known selectable markers such as neomycin resistance, ampicillin resistance, tetracycline resistance, chloramphenicol resistance, kanamycin resistance, and the like.

Where a parent host cell has been genetically modified to produce two or more ACBP6s, nucleotide sequences encoding the two or more ACBP6s will in some embodiments each be contained on separate expression vectors. Where the host cell is genetically modified to express one or more ACBP6s, nucleotide sequences encoding the one or more ACBP6s will in some embodiments be contained in a single expression vector. Where nucleotide sequences encoding the one or more ACBP6s are contained in a single expression vector, in some embodiments, the nucleotide sequences will be operably linked to a common control element (for example, a promoter), such that the common control element controls expression of all of the ACBP6-encoding nucleotide sequences on the single expression vector.

Where nucleotide sequences encoding ACBP6(s) are contained in a single expression vector, in some embodiments, the nucleotide sequences will be operably linked to different control elements (for example, a promoter), such that, the different control elements control expression of each of the ACBP6-encoding nucleotide sequences separately on a single expression vector.

A subject screening method can involve introducing an exogenous nucleic acid into a host cell, producing a test cell, where the host cell is one that exhibits growth inhibition in low-temperature conditions when the temperature of the culture conditions is lowered to a growth-inhibiting level for a growth-inhibiting period of time. When an exogenous nucleic acid comprising a nucleotide sequence that encodes an ACBP6 is introduced into the host cell, growth inhibition of the test cell is relieved. Thus, a reduction in growth inhibition indicates that the exogenous nucleic acid encodes an ACBP6, where the encoded ACBP6 is produced at a level and/or has an activity that relieves the low-temperature-induced growth inhibition. A reduction in growth inhibition includes an at least about 10%, at least about 20%, at least about 30%, at least about 40%, at least about 50%, at least about 60%, at least about 70%, at least about 80%, at least about 90%, or more, reduction in growth inhibition as compared to a non-genetically-modified host. In some embodiments, the ACBP6 encoded by the exogenous nucleic acid reduces the growth inhibition such that the rate of cell growth is restored to the rate of cell growth of the host cell when grown under conditions where temperature is not lowered to a growth inhibiting level.

In some embodiments, for example, where the exogenous nucleic acid is a plurality of exogenous nucleic acids (such as, for example, a cDNA library, a genomic library, or a population of nucleic acids, each encoding an ACBP6 with a different amino acid sequence, etc.), the exogenous nucleic acids are introduced into a plurality of host cells, forming a plurality of test cells. The test cells are in some embodiments grown in culture under conditions such that the temperature is lowered in a growth inhibiting and/or death-inducing amount; those test cells comprising an exogenous nucleic acid that comprises nucleotide sequences encoding an ACBP6 will grow faster than test cells that do not comprise an exogenous nucleic acid that comprises nucleotide sequences encoding an ACBP6, or those test cells comprising an exogenous nucleic acid that comprises nucleotide sequences encoding an ACBP6 will live, while test cells that do not comprise an exogenous nucleic acid that comprises nucleotide sequences encoding ACBP6 will die or otherwise be adversely affected.

In some embodiments, the method further involves isolating an exogenous nucleic acid from a test cell, where the exogenous nucleic acid is one that that relieves growth inhibition in a subject screening method. Methods of isolating the exogenous nucleic acid from a test cell are well known in the art. Suitable methods include, but are not limited to, any of a number of alkaline lysis methods that are standard in the art.

In some embodiments, a subject screening method will further comprise further characterizing a candidate gene product. In these embodiments, the exogenous nucleic acid comprising nucleotide sequence(s) encoding an ACBP6(s) are isolated from a test cell; the gene product(s) are expressed in a cell and/or in an in vitro cell-free transcription/translation system. In some embodiments, the exogenous nucleic acid is subjected to nucleotide sequence analysis, and the amino acid sequence of the gene product deduced from the nucleotide sequence. In some embodiments, the amino acid sequence of the gene product is compared with other amino acid sequences in a public database of amino acid sequences, to determine whether any significant amino acid sequence identity to an amino acid sequence of a known protein exists. In addition, the gene product(s) are expressed in a cell and/or in an in vitro cell-free transcription/translation system; and the effect of the gene product(s) on a metabolic pathway intermediate or other metabolite is analyzed.

Exogenous nucleic acids that are suitable for introducing into a host cell, to produce a test cell, include, but are not limited to, naturally-occurring nucleic acids isolated from a cell; naturally-occurring nucleic acids that have been modified (for example, by mutation) before or subsequent to isolation from a cell; synthetic nucleic acids, e.g., nucleic acids synthesized in a laboratory using standard methods of chemical synthesis of nucleic acids, or generated by recombinant methods; synthetic or naturally-occurring nucleic acids that have been amplified in vitro, either within a cell or in a cell-free system; and the like.

Exogenous nucleic acids that are suitable for introducing into a host cell include, but are not limited to, genomic DNA; RNA; a complementary DNA (cDNA) copy of mRNA isolated from a cell; recombinant DNA; and DNA synthesized in vitro, e.g., using standard cell-free in vitro methods for DNA synthesis. In some embodiments, exogenous nucleic acids are a cDNA library made from cells, either prokaryotic cells or eukaryotic cells. In some embodiments, exogenous nucleic acids are a genomic DNA library made from cells, either prokaryotic cells or eukaryotic cells.

Nucleic acids will in some embodiments be mutated before being introduced into a host cell. Methods of mutating a nucleic acid are well known in the art and include well-established chemical mutation methods, radiation-induced mutagenesis, and methods of mutating a nucleic acid during synthesis. Chemical methods of mutating DNA include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, .gamma.-irradiation, X-rays, and fast neutron bombardment. Mutations can also be introduced into a nucleic acid using, e.g., trimethylpsoralen with ultraviolet light. Random or targeted insertion of a mobile DNA element, e.g., a transposable element, is another suitable method for generating mutations. Mutations can be introduced into a nucleic acid during amplification in a cell-free in vitro system, e.g., using a polymerase chain reaction (PCR) technique such as error-prone PCR. Mutations can be introduced into a nucleic acid in vitro using DNA shuffling techniques (e.g., exon shuffling, domain swapping, and the like). Mutations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Methods of mutating nucleic acids are well known in the art, and any known method is suitable for use. See, e.g., Stemple (2004) *Nature* 5:1-7; Chiang et al. (1993) *PCR Methods Appl* 2(3): 210-217; Stemmer (1994) *Proc. Natl. Acad. Sci. USA* 91:10747-10751; and U.S. Pat. Nos. 6,033,861, and 6,773, 900.

In many embodiments, the exogenous nucleic acid is inserted into an expression vector. Expression vectors that are suitable for use in prokaryotic and eukaryotic host cells are known in the art, and any suitable expression vector can be used. Suitable expression vectors are as described above.

As noted above, an exogenous nucleic acid will in some embodiments be isolated from a cell or an organism in its natural environment. In some embodiments, the nucleic acid of the cell or organism will be mutated before nucleic acid is isolated from the cell or organism. In other embodiments, the exogenous nucleic acid is synthesized in a cell-free system in vitro.

In some embodiments, the exogenous nucleic acid is a synthetic nucleic acid. In some embodiments, a synthetic nucleic acid comprises a nucleotide sequence encoding a variant ACBP6, for example, an ACBP6 that differs in amino acid sequence by one or more amino acids from a naturally-occurring *Arabidopsis* ACBP6 or other parent ACBP6. In some embodiments, a variant ACBP6 differs in amino acid sequence by one amino acid, two amino acids, three amino acids, four amino acids, five amino acids, six amino acids, seven amino acids, eight amino acids, nine amino acids, or amino acids, or more, compared to the amino acid sequence of a naturally-occurring parent ACBP. In some embodiments, a variant ACBP differs in amino acid sequence by from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 50 amino acids, or from about 50 amino acids to about 60 amino acids, compared to the amino acid sequence of a naturally-occurring parent ACBP.

In some embodiments, a variant ACBP6 is encoded by a nucleic acid that hybridizes under stringent hybridization conditions to a nucleic acid encoding an *Arabidopsis* or other known ACBP. In other embodiments, a variant ACBP6 is encoded by a nucleic acid that hybridizes under moderate hybridization conditions to a nucleic acid encoding an *Arabidopsis* or other known ACBP.

In some embodiments, a nucleic acid comprising a nucleotide sequence encoding a naturally-occurring ACBP is mutated, using any of a variety of well-established methods, giving rise to a nucleic acid comprising a nucleotide sequence encoding a variant ACBP6. Suitable mutagenesis methods include, but are not limited to, chemical mutation methods, radiation-induced mutagenesis, and methods of mutating a nucleic acid during synthesis, as described supra. Thus, for example, a nucleic acid comprising a nucleotide sequence encoding a naturally-occurring ACBP is exposed to a chemical mutagen, as described above, or subjected to radiation mutation, or subjected to an error-prone PCR, and the mutagenized nucleic acid introduced into a genetically modified host cell(s) as described above. Methods for random mutagenesis using a "mutator" strain of bacteria are also well known in the art and can be used to generate a variant ACBP. See, e.g., Greener et al., "An Efficient Random Mutagenesis Technique Using an *E. coli* Mutator Strain", *Methods in Molecular Biology*, 57:375-385 (1995). Saturation mutagenesis techniques employing a polymerase chain reaction (PCR) are also well known and can be used. See, e.g., U.S. Pat. No. 6,171,820. Nucleic acids comprising a nucleotide sequence encoding a variant ACBP are identified by the ability to relieve growth inhibition caused by lead.

Nucleotide sequences encoding ACBPs are known in the art, and any known ACBP6-encoding nucleotide sequence can be altered to generate a synthetic nucleic acid for use in a subject method.

An embodiment of the invention provides a host cell comprising a vector according to the invention. Other embodiments include plant plastid transformation vectors or nuclear transformation vectors containing nucleotide sequences encoding *Arabidopsis* ACBP6, such as containing the full-length ACBP6, or variants or fragments thereof, for the expression of ACBP6s conveying similar low-temperature tolerance activities to full-length ACBP6. These plant vectors may contain other sequences for the generation of chimeric ACBP6 polypeptides which may contain mutations, deletions, or insertions of the ACBP6 polypeptides.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a genetically modified host cell" includes a plurality of such host cells and reference to "the ACBP6" includes reference to one or more ACBP6s and equivalents thereof that will become known to those skilled in the art in view of this disclosure, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

According to embodiments of the present invention, a wide variety of plants and plant cell systems can be engineered for the desired physiological and agronomic characteristics described herein using the nucleic acid constructs of the present invention by various transformation methods known in the art, including *Agrobacterium*-mediated transformation (Horsch et al., Science 227: 1227-1231, 1985) or plastid transformation (Staub and Maliga, *Plant J.* 6: 547-553, 1994; Hahn and Kuehnle, 2003, cited herein above). In preferred embodiments, target plants and plant cells for engineering include, but are not limited to, those monocotyledonous and dicotyledonous plants, such as crops including grain crops (for example, wheat, maize, rice, millet, barley), tobacco, fruit crops (for example, tomato, strawberry, orange, grapefruit, banana), forage crops (for example, alfalfa), root vegetable crops (for example, carrot, potato, sugar beets, yam), leafy vegetable crops (for example, lettuce, spinach); flowering plants (for example, petunia, rose, chrysanthemum), conifers and pine trees (for example, pine fir, spruce); oil crops (for example, sunflower, rape seed); and plants used for experimental purposes (for example, *Arabidopsis*).

According to other embodiments of the present invention, desired plants may be obtained by engineering one or more of the vectors expressing ACBP6s as described herein into a variety of plant cell types, including but not limited to, protoplasts, tissue culture cells, tissue and organ explants, pollens, embryos, as well as whole plants. In an embodiment of the present invention, the engineered plant material is selected or screened for transformants (those that have incorporated or integrated the introduced gene construct(s)) following the approaches and methods described below. An isolated transformant may then be regenerated into a plant and progeny thereof (including the immediate and subsequent generations) via sexual or asexual reproduction or growth. Alternatively, the engineered plant material may be regenerated into a plant before subjecting the derived plant to selection or screening for the marker gene traits. Procedures for regenerating plants from plant cells, tissues or organs, either before or after selecting or screening for marker gene(s), are well known to those skilled in the art.

According to another embodiment of the present invention, tissue-specific promoters may be used to target the expression of ACBP6s in fruits, roots or leaves so that an edible plant part is provided low-temperature tolerance. Examples of tissue-specific promoters include those encoding rbsC (Coruzzi et al., *EMBO J.* 3:1671-1697, 1984) for leaf-specific expression and SAHH or SHMT (Sivanandan et al., *Biochimica et Biophysica Acta* 1731:202-208, 2005) for root-specific expression. Another exemplary root-specific promoter is taught by Ekramoddoullah et al., U.S. Pat. No. 7,285,656 B2. Also, the Cauliflower Mosaic Virus (CaMV) 35S promoter has been reported to have root-specific and leaf-specific modules in its promoter region (Benfey et al., *EMBO J.* 8:2195-2202, 1989). Other tissue-specific promoters are well known and widely available to those of ordinary skill in the art. Further, a wide variety of constitutive or inducible promoters are also well known and widely available to those of ordinary skill in the art.

A transformed plant cell, callus, tissue, or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or Cl genes) that may be present on the vector of the present invention. Such selection and screening methodologies are well known to those skilled in the art. Alternatively or in addition, screening may be for improved low-temperature tolerance as taught herein, for example, by observing a reduction in growth-inhibition.

Physical and biochemical methods may also be used to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme activity, where such gene products are encoded by the gene construct; 4) protein gel electrophoresis (PAGE), Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art. In a specific embodiment, the selectable marker gene nptII, which specifies kanamycin-resistance, is used in nuclear transformation.

Examples of plants are monocots, dicots, crop plants (i.e., any plant species grown for purposes of agriculture, food production for animals including humans, plants that are typically grown in groups of more than about 10 plants in order to harvest the entire plant or a part of the plant, for example, a fruit, a flower or a crop, for example, tobacco, grain, that the plants bear, etc.), trees (i.e., fruit trees, trees grown for wood production, trees grown for decoration, etc.), flowers of any kind (i.e., plants grown for purposes of decoration, for example, following their harvest), cactuses. Further examples of plants in which the ACBP6s may be expressed include Viridiplantae, Streptophyta, Embryophyta, Tracheophyta, Euphyllophytes, Spermatophyta, Magnoliophyta, Liliopsida, Commelinidae, Poales, Poaceae, *Oryza, Oryza sativa, Zea, Zea mays, Hordeum, Hordeum vulgare, Triticum, Triticum aestivum*, Eudicotyledons, Core eudicots, Asteridae, Euasterids, Rosidae, Eurosids H, Brassicales, Brassicaceae, *Arabidopsis, Magnoliopsida*, Solananae, Solanales, Solanaceae, *Solanum*, and *Nicotiana*. Thus, the embodiments of the invention have uses over a broad range of plants including, but not limited to, species from the genera. *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Panneserum, Persea, Phaseolus, Pistachia, Pisum, Pyrus, Prunus, Raphanus, Ricinus, Secale, Senecio, Sinapis, Solanum, Sorghum, Theobromus, Trigonella, Titicum, Vicia, Vitis, Vigna*, and *Zea*.

We have discovered from both northern blot analysis and western blot analysis that the expression of *Arabidopsis* ACBP6 is induced by cold treatment. We showed that alterations in ACBP6 expression in the acbp6 knockout mutant and ACBP6-overexpressing transgenic *Arabidopsis*, culminated in decreased and enhanced freezing tolerance, respectively. ACBP6-mediated freezing tolerance was not dependent on induction of COR gene expression. Instead, it was accompanied by increased phospholipase PLDδ expression, decreased PC content, and increased PA production, indicating that ACBP6 enhanced freezing tolerance via the PLDδ-mediated pathway. In wild-type *Arabidopsis*, it has been demonstrated that freezing is accompanied by decreases in many species of PC, PE and PG, but increases in their metabolites, PA and lysophospholipids (Welti et al., J Biol Chem 277: 31994-32002, 2002). In wild-type *Arabidopsis*, it has been demonstrated that freezing is accompanied by decreases in many species of PC, PE and PG, but increases in their metabolites, PA and lysophospholipids (Welti et al., J Biol Chem 277: 31994-32002, 2002). PLDδ and PLDα1 are two phospholipases that produce PA from phospholipids; they play a positive role and a negative role, respectively, in mediating freezing tolerance (Welti et al., J Biol Chem 277: 31994-32002, 2002; Zhang et al., Proc Natl Acad Sci USA 101: 9508-9513, 2004; Li et al., Nat Biotechnol 22: 427-433, 2004; Rajashekar et al., J Plant Physiol 163: 916-926, 2006; Li et al., J Biol Chem 283: 461-468, 2008). Upon freezing treatment, the PLDα1 mutant displays enhanced freezing tolerance accompanied by decreases in freezing-induced hydrolysis of PC and therefore generated less PA (Zhang et al., Proc Natl Acad Sci USA 101: 9508-9513, 2004; Rajashekar et al., J Plant Physiol 163: 916-926, 2006; Li et al., J Biol Chem 283: 461-468, 2008). Increased freezing ($-12°$ C.) sensitivity was observed in the PLDδ knockout mutant while transgenic *Arabidopsis* overexpressing PLDδ are freezing tolerant and show elevated PA production (Li et al., Nat Biotechnol 22: 427-433, 2004). The enhanced freezing tolerance accompanied by PA accumulation upon freezing treatment in ACBP6-overexpressors is consistent with previous observations of PLDδ-overexpressors. Our comparison of the increases in various PA species of freezing-treated PLDδ- and ACBP6-overexpressing transgenic plants revealed that they show similarities in the elevated production of 34:2-, 34:3-, 36:5- and 36:6-PA. In ACBP6-overexpressors, all increases in PA species were correlated with decreases in corresponding PC species, suggesting that these PA accumulations were primarily derived from PC. Consistent with lipid profiling results, irrespective of NA, CA, freezing or thawing stages, PLDδ expression was comparably higher in the ACBP6-overexpressors than wild type. Down-regulation of PLDδ expression in the acbp6 mutant subsequently resulted in enhanced freezing sensitivity. ACBP6-mediated freezing tolerance appears to be closely related to increased PLDδ expression and its consequential action on PC. PLDδ is known to mediate freezing tolerance by stabilizing membranes through its interaction with the cytoskeleton, and that the PA it produces (which constitutes about 20% of the total PA generated during freezing) not only promotes a non-lamellar phase membrane lipid but inhibits phospholipase A activity (Li et al., Nat Biotechnol 22: 427-433, 2004; J Biol Chem 283: 461-468, 2008). Comparison in the expression profiles of PLDδ (Katagiri et al., Plant J 26: 595-605, 2001) with ACBP6 indicated that they are both expressed in leaves, roots, stalks and flowers, suggesting feasibility of their interaction in phospholipid metabolism within these organs.

In tests with His-tagged ACBP6 using filter-binding assays to examine its binding to phospholipids, we observed that ACBP6 binds PC, not PA or LysoPC, implicating a role for ACBP6 in phospholipid metabolism in *Arabidopsis*. ACBP6 possibly participates in phospholipid metabolism by regulating PLDδ expression, resembling the yeast 10-kD ACBP which controls genes encoding proteins involved in stress responses as well as in fatty acid and phospholipid synthesis (Feddersen et al., Biochem J 407: 219-230, 2007). These stress-related proteins would include catalase and heat-shock proteins while those related to lipid metabolism include OLE1 (stearoyl-CoA desaturase), INO1 (Myo-inositol-3-phosphate synthase), PSD1 (PS decarboxylase 1), PSD2 (PS decarboxylase 2), CHO2 (PE N-methyltransferase) and OPI3 (methylene-fatty-acyl-phospholipid synthase). Furthermore, the yeast ACBP-acyl-CoA ester complex can modulate gene regulation and other cellular processes by donation of acyl-CoA esters (Feddersen et al., Biochem J 407: 219-230, 2007). In ACBP6-overexpressors the induced expression of PLDδ may be a consequence of similar sequestering action by ACBP6. Since ACBP6 binds PC (Chen et al., Plant Physiol 148: 304-315) and acyl-CoAs (Engeseth et al., Arch Biochem Biophys 331: 55-62, 1996), it can possibly maintain an intracellular PC or acyl-CoA pool that participates in the regulation of genes including PLDδ and/or their corresponding proteins. It has already been shown that fatty acids and their derivatives regulate gene expression in bacteria, yeast and mammals (Kliewer et al., Proc Natl Acad Sci 94: 4318-4323, 1997; Black et al., J Nutr 130: 305S-309S, 2000).

It is reasonable to assume that due to the high conservation of 10-kD ACBPs amongst species, functions such as maintenance of intracellular cytosolic lipid pools and gene regulation may remain common to these 10-kD proteins. For example, the *Arabidopsis* 10 kD homolog retains a function in the binding and protection of oleoyl-CoA from degradation by microsomal acyl hydrolases (Engeseth et al., Arch Biochem Biophys 331: 55-62, 1996). If ACBP6 were involved in gene regulation, two other cytosolic ACBPs (ACBP4 and ACBP5) in *Arabidopsis* can potentially shuttle acyl-CoAs from the chloroplast to the ER. Since the dissociation constants ($K_d$ values) for recombinant $(His)_6$-ACBP4, $(His)_6$-ACBP5 and $(His)_6$-ACBP6 in binding oleoyl-CoA esters are $5.6\times10^{-7}$ M, $6.8\times10^{-7}$ M and $3.7\times10^{-6}$ M, respectively, ACBP4 and ACBP5 likely play a more significant role than ACBP6 in this transfer (Xiao et al., Plant Physiol Biochem 47: 926-933, 2009). The lack of difference in galactolipid compositions under normal growth conditions at 23° C. between wild type and ACBP6-overexpressors, as revealed from lipid analysis of rosettes, suggest that ACBP6 may not be involved in oleoyl-CoA transfer from the chloroplasts, but instead, it mediates freezing stress responses associated with phospholipid metabolism. Its ability to bind PC demonstrates it can transport intracellular PC within the cytosol.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); and the like.

In the examples using FIGS. 1-7, the related description in the text have been reproduced from Chen et al. 2008; Plant Physiology 148: 304-315 (www.plantphysiol.org; copyright American Society of Plant Biologists).

Example 1

ACBP6 is a Cytosolic Protein

Figure 1B:
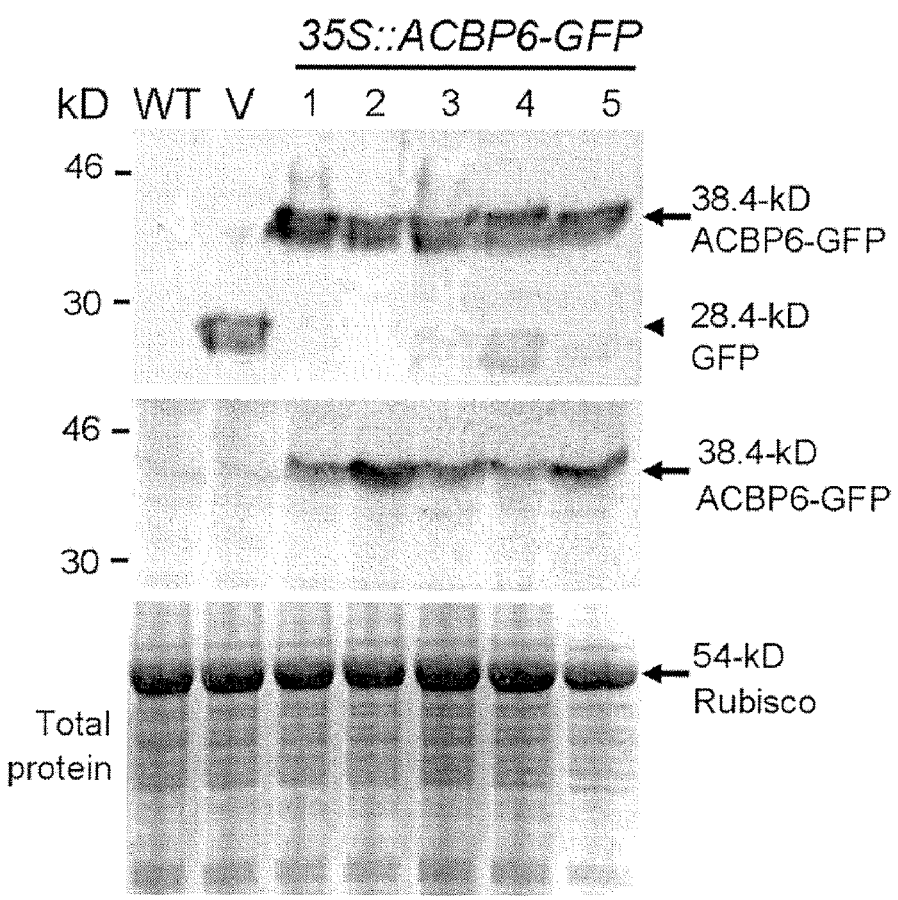
Figure 1C:
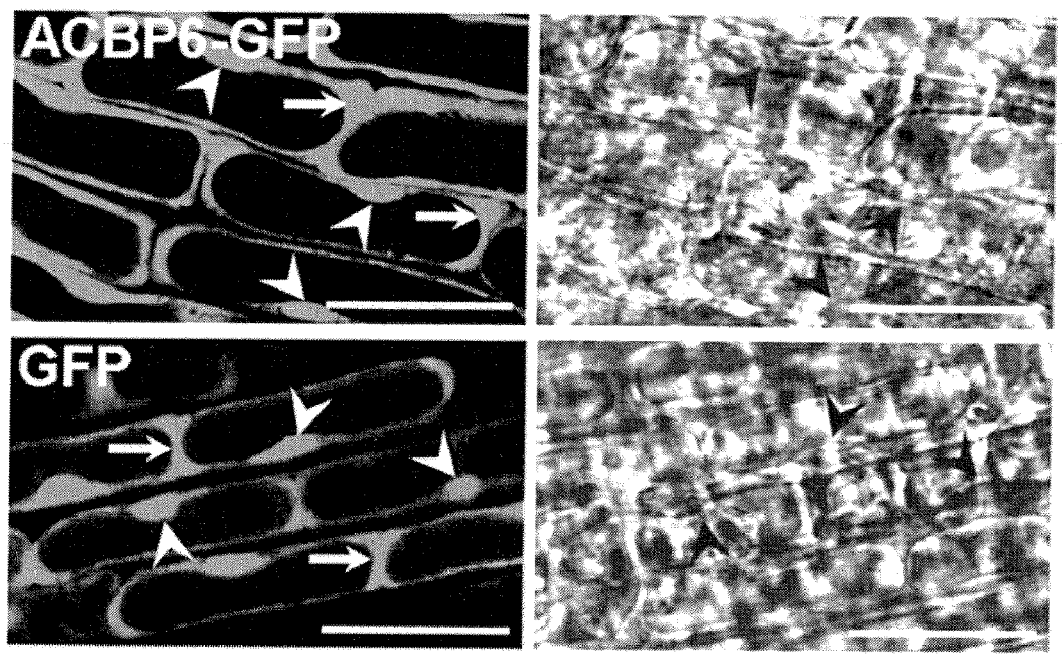
Figure 1D:
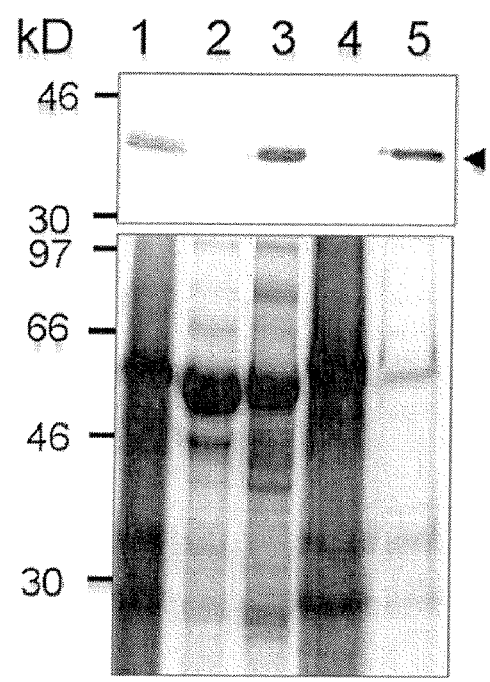

ACBP6 was predicted to be localized to the cytosol by PSORT analysis (http://psort.nibb.ac.jp). A 35S::ACBP6-GFP construct was generated by fusing the ACBP6 coding region to the autofluorescent protein tag, eGFP in vector pBI-eGFP (Shi et al., *Plant Cell* 17: 2340-2354.2005) for expression from the Cauliflower Mosaic Virus (CaMV) 35S promoter. Transgenic *Arabidopsis* lines expressing 35S:: ACBP6-GFP (SEQ. ID No: 6) were obtained using *Agrobacterium*-mediated transformation. Expression of the 1.3-kb ACBP6-GFP mRNA in 5 independent 35S::ACBP6-GFP transformants was detected in northern blot analysis using an ACBP6 cDNA probe which also hybridized to the endogenous 0.6-kb ACBP6 mRNA (FIG. 1A). The expression of the 38.4-kD ACBP6-GFP (SEQ. ID No: 7, consisting of 10.4-kD ACBP6 fused to 28-kD GFP) in these five lines was confirmed in western blot analyses using anti-GFP and anti-ACBP6 antibodies (FIG. 1B). Subsequently when premature root cells of 2-week-old $T_2$ transgenic *Arabidopsis* seedlings from 35S::ACBP6-GFP line 1 were examined by confocal laser scanning microscopy, fluorescence was detected primarily in the cytosol, with some signals in the nuclei (white arrowheads in FIG. 1C top). Expression in both nuclei and cytosol were observed in the GFP control (FIG. 1C, bottom).

Figure 1E:
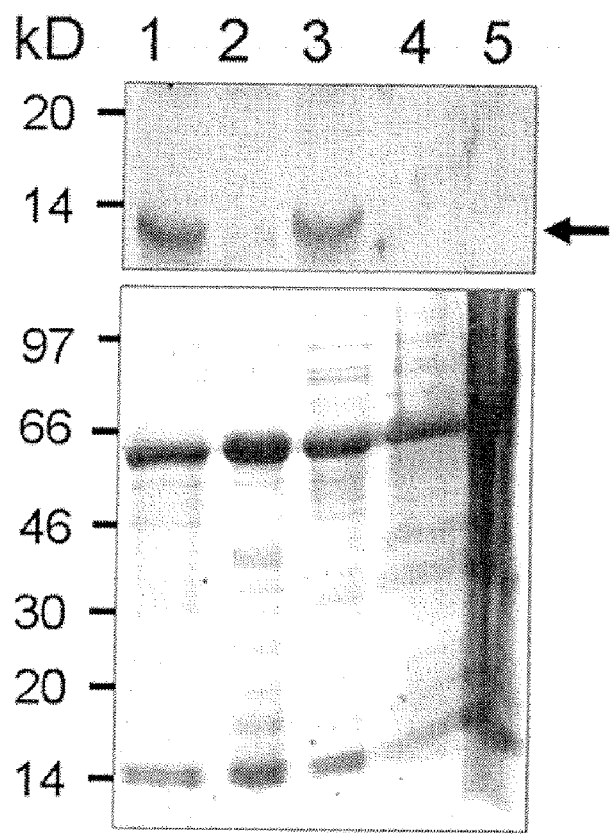

On western blot analysis (FIG. 1D) with anti-GFP antibodies of subcellular fractions of protein from rosette leaves from 35S::ACBP6-GFP line 1, a cross-reacting 38.4-kD ACBP6-GFP band was observed in total protein (lane 1) as well as in the cytosolic (lane 3) and nuclear (lane 5) fractions. No such band was evident in the membrane fraction (lane 2) and the fraction containing large particles including mitochondria, chloroplasts and peroxisomes (lane 4). Since the nuclear localization of ACBP6-GFP overexpressed from the 35S:: ACBP6-GFP line could be due to the size of ACBP6-GFP (38.4 kD) being smaller than the size exclusion limit (~40 to 60 kD) for passive diffusion through nuclear pore complexes (Gorlich and Mattaj, Science 271: 1513-1518, 1996; Li et al., Plant Physiol 141: 527-539, 2006), it was pertinent to determine the subcellular localization of native ACBP6. Subcellular fractions of protein from rosette leaves from wild-type (Col-0) *Arabidopsis*, obtained following differential centrifugation, were then analyzed in western blot analysis using ACBP6-specific antibodies (FIG. 1E). A cross-reacting 10.4-kD ACBP6 band in total protein (lane 1, FIG. 1E) and in the cytosolic (lane 3) fraction. Lack of this hand in the membrane fraction (lane 2), the fraction containing large particles including mitochondria, chloroplasts and peroxisomes (lane 4) and the nuclear fraction (lane 5) confirmed that ACBP6 is a cytosolic protein and that ACBP6-GFP had diffused into the cell nuclei of transgenic *Arabidopsis* overexpressing ACBP6-GFP. Hence, unlike some mammalian 10-kD ACBPs which directly interact with nuclear factors in the nuclei (Petrescu et al., *J Biol Chem* 278: 51813-51824, 2003), ACBP6 seems to be confined to the cytosol, consistent with its predicted localization and its lack of a nuclear targeting signal.

Example 2

ACBP6 mRNA and Protein are Induced by Cold Treatment

Figure 2A:
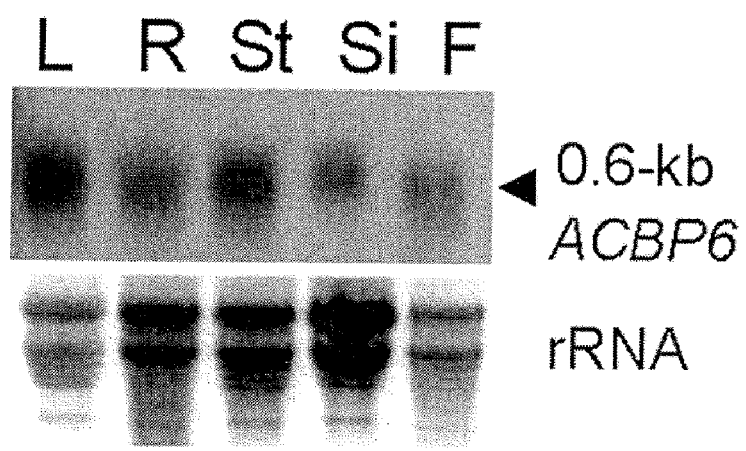
Figure 2B:
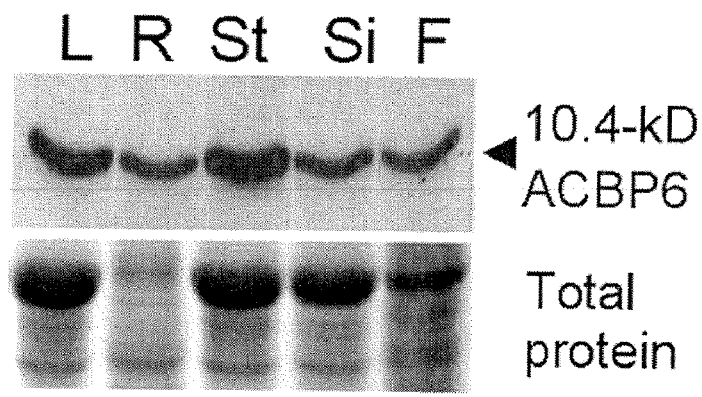
Figure 2C:
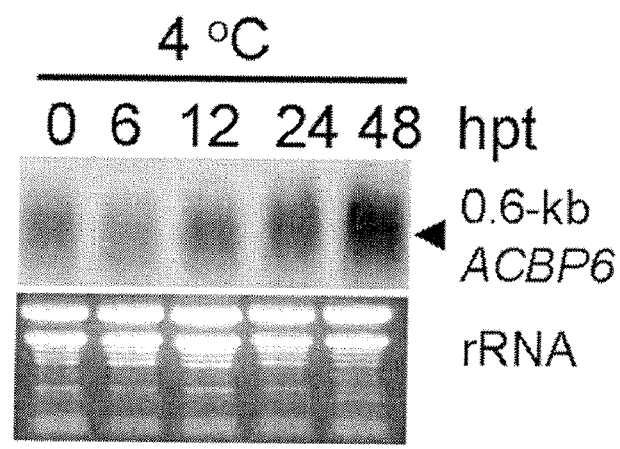
Figure 2D:
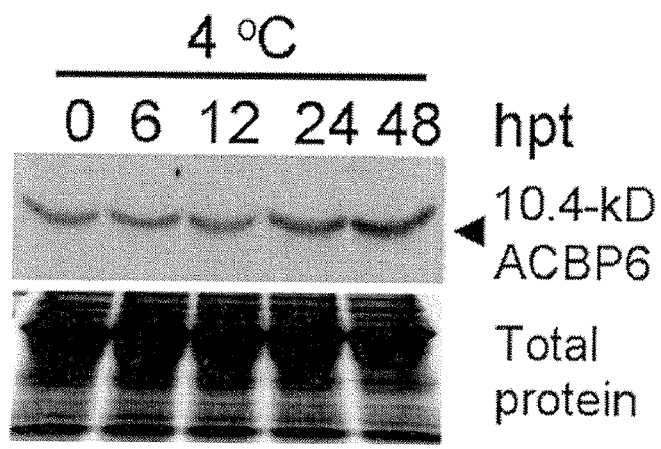

The spatial pattern of ACBP6 expression was investigated by northern blot analyses using total RNAs extracted from various organs. Northern blot analysis was also used to analyze the response of ACBP6 expression to various forms of biotic and abiotic stresses. ACBP6 mRNA was more highly expressed in leaves and stalks compared to roots, flowers and siliques (FIG. 2A). A similar pattern in distribution of ACBP6 protein was observed in western blot analysis using ACBP6-specific antibodies (FIG. 2B). ACBP6 mRNA was cold-induced (FIG. 2C) but was not induced by treatments using fungal elicitor (arachidonic acid), high salt and methyl jasmonate in whole plants (data not shown). Absence of induction with high salt and methyl jasmonate treatments in northern blot with analysis is consistent with data from microarray analysis on ACBP6 (At1g31812) expression. Northern blot analysis using total RNA from 4-week-old wild-type *Arabidopsis* exposed to 4° C. for 0, 6, 12, 24 and 48 h, showed that ACBP6 mRNA increased following cold treatment and was most significant at 48 h post-treatment (FIG. 2C). Western blot analysis (FIG. 2D) demonstrated that ACBP6 protein showed highest accumulation 48 h after cold treatment. Microarray data did not show cold-induction of ACBP6 expression in microarrays at 24 h after 4° C. treatment and microarray data was not available for a period exceeding 24 h.

Example 3

Characterization of an acbp6 Knockout Mutant

Figure 3A:
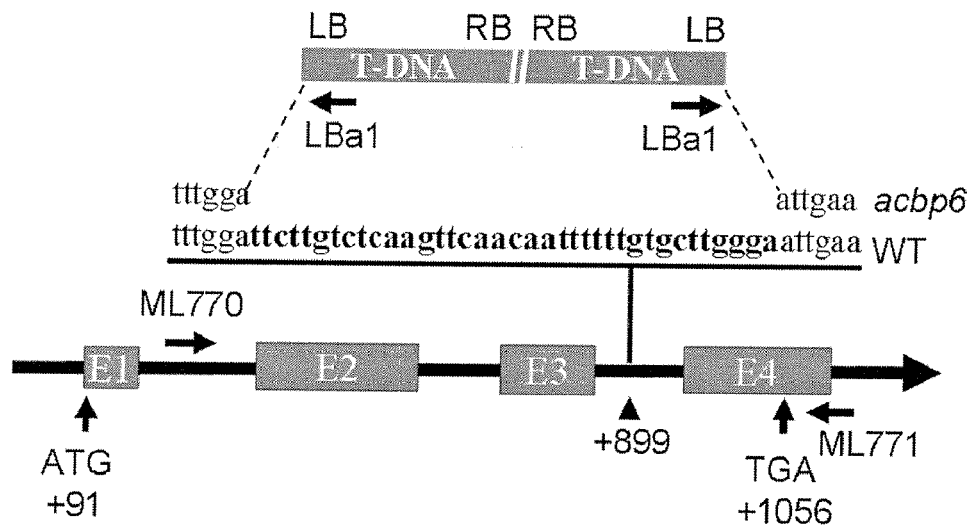
Figure 3B:
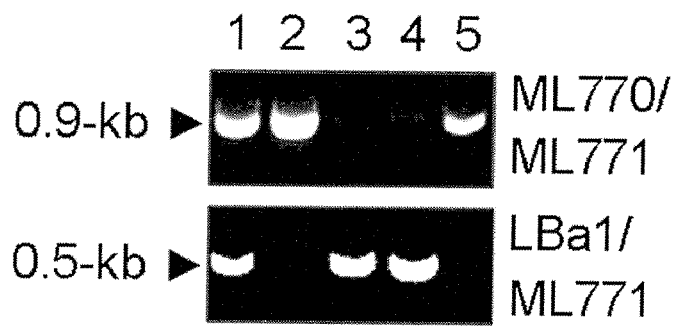

An acbp6 T-DNA knockout mutant (SALK_104339) was obtained from the *Arabidopsis* Information Resource (TAIR) to further investigate the function of ACBP6 upon cold treatment. The mutant was subsequently characterized. The T-DNA insert in ACBP6 in the acbp6 homozygous mutant was confirmed by the Polymerase Chain Reaction (PCR) using gene-specific primers (ML770 and ML771) and a T-DNA border primer, LBa1 (FIG. 3A). On PCR analysis using ML770/ML771 (FIG. 3B, top panel), a 0.9-kb band was amplified from wild-type *Arabidopsis* (lanes 2 and 5) and the acbp6 heterozygous mutants (lane 1) but not homozygous mutants (lanes 3 and 4). When LBa1/ML771 primers were used in PCR (FIG. 3B, bottom panel), a 0.5-kb band was observed in the acbp6 heterozygous (lane 1) and homozygous mutants (lanes 3 and 4) but not in wild type (lanes 2 and 5).

Figure 3C:
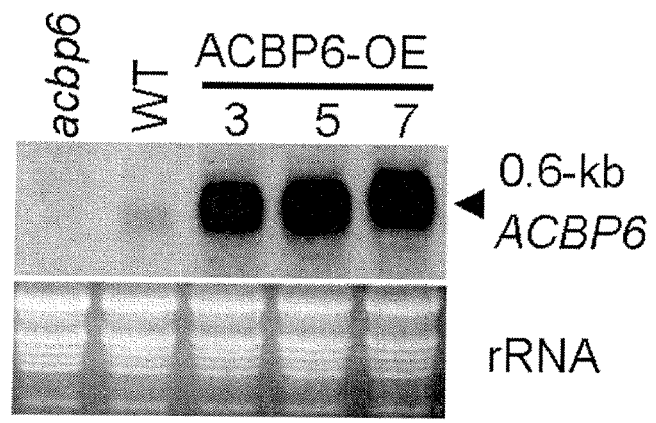
Figure 3D:
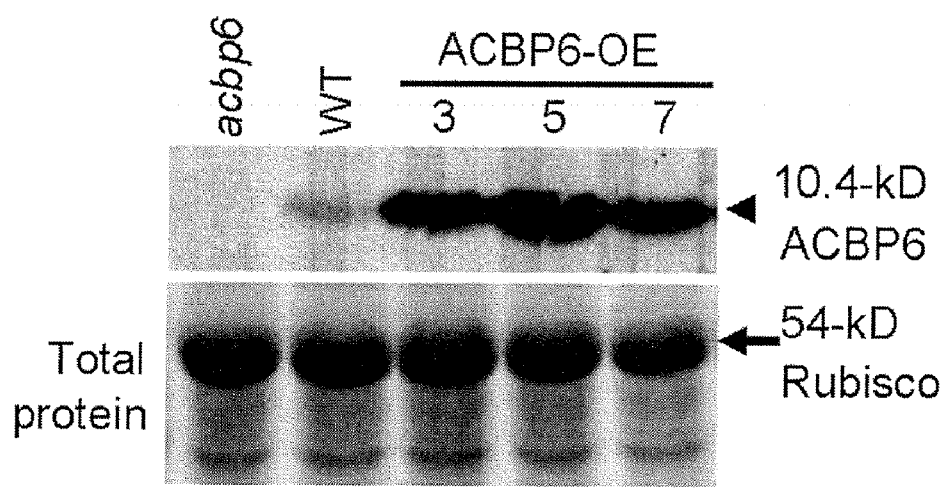

Results from DNA sequence analysis of the PCR products spanning the junctions between ACBP6 and the T-DNA showed that the T-DNA was inserted in the third intron of ACBP6, resulting in a 37-bp deletion in ACBP6 (FIG. 3A). Northern blot analysis showed that transcription of ACBP6 was disrupted in the acbp6 homozygous mutant, while a 0.6-kb mRNA was detected in wild-type *Arabidopsis* (FIG. 3C). The 10.4-kD ACBP6 cross-reacting band was present in wild type but was absent in the homozygous mutant on western blot analysis, confirming that the mutant is a knockout line (FIG. 3D).

Example 4

Generation of ACBP6-Overexpressing Transgenic *Arabidopsis* Lines

Transgenic *Arabidopsis* plants overexpressing ACBP6 were generated by *Agrobacterium*-mediated transformation (Clough and Bent, Plant J 16: 735-743, 1998) and resultant transformants were subsequently used to test whether ACBP6 overexpression enhances cold-tolerance. The ACBP6 full-length cDNA (SEQ. ID No: 1) was expressed from the CaMV 35S promoter in binary vector pSMB (Mylne and Botella, Physiol Plant 15: 473-497, 1998) for transformation of *Ara-* bidopsis (Col-0). Three independent T$_2$ ACBP6 overexpressor lines (OE-3, OE-5 and OE-7) were identified to overexpress the 0.6-kb ACBP6 mRNA in northern blot analysis (FIG. 3C) and to accumulate the 10.4-kD ACBP6 protein in western blot analysis (FIG. 3D).

Example 5

Figure 4A:
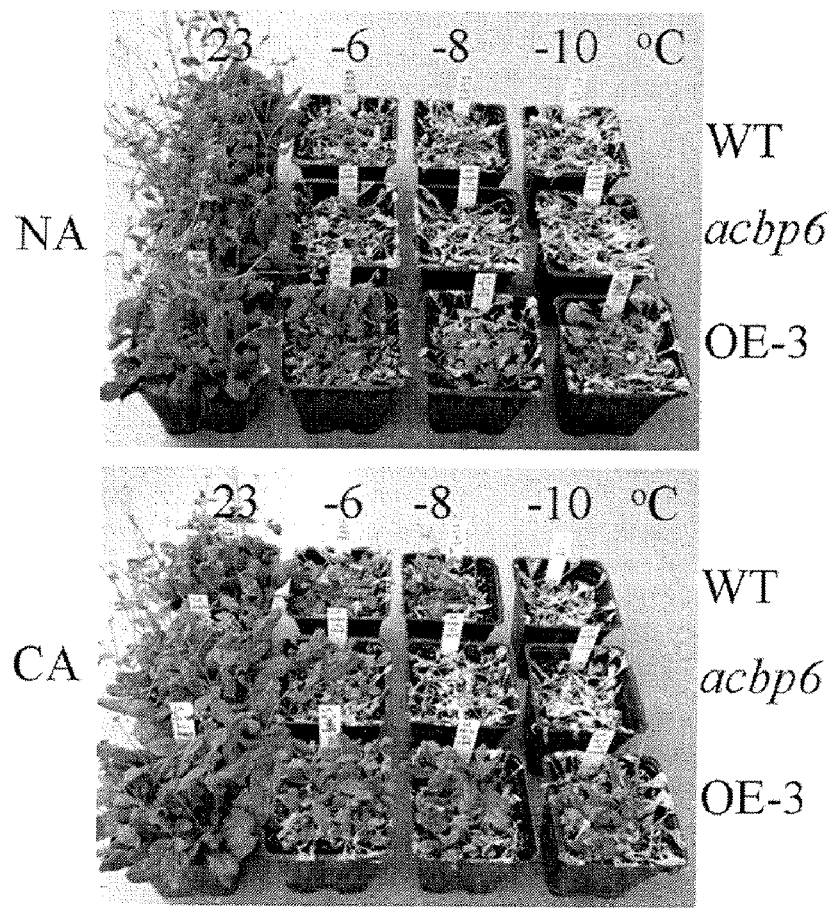

The acbp6 Mutant is More Sensitive to Freezing Stress while ACBP6-Overexpressors are Freezing Tolerant To investigate the effects of the ACBP6 mutation and ACBP6 overexpression on freezing tolerance, 5-week-old wild type, acbp6 mutant and ACBP6-overexpressors from nonacclimated (NA) and cold-acclimated (CA) sets were examined. Few wild-type and acbp6 plants tolerated freezing temperatures at −6° C., −8° C. and −10° C. without cold acclimation (FIG. 4A) but The majority of ACBP6-overexpressor (OE-3) plants survived in freezing temperature as low as −6° C. and 45% (P<0.05) of them survived even at −8° C. and −10° C. (FIG. 4A, upper image). Following cold acclimation at 4° C. for 3 days, freezing tolerance was enhanced in all three genotypes. More CA wild-type plants than CA mutants survived at −8° C.; all CA acbp6 mutants did not survive at −8° C. (FIG. 4A, lower image). However, CA ACBP6-overexpressor (OE-3) plants tolerated freezing stress at −8° C. and −10° C. better than CA wild-type or mutant plants and NA OE-3 plants (FIG. 4A).

Figure 4B:
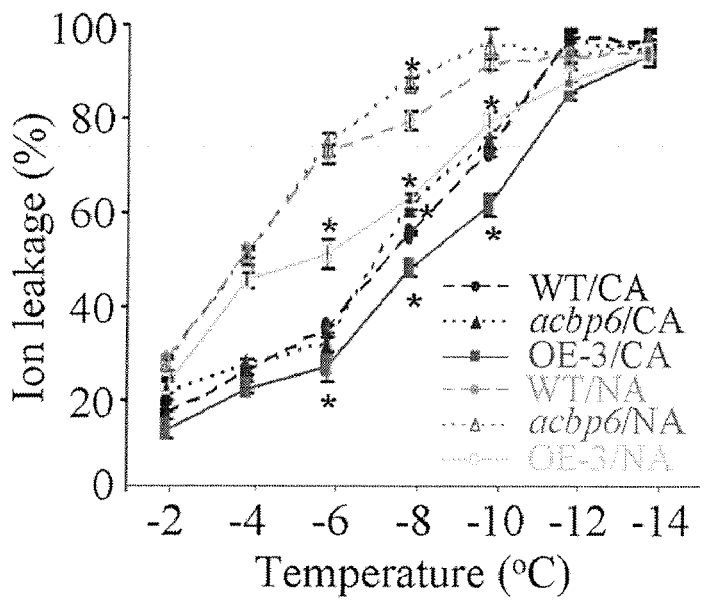

Electrolyte leakage was measured using both NA and CA freezing-treated leaves from wild type, acbp6 mutant and ACBP6-overexpressor to evaluate freezing injury after freezing treatment. Ionic leakage following treatment at −8° C. was observed to be significantly greater in both NA and CA acbp6 mutants than corresponding NA and CA wild type (P<0.05) (FIG. 4B). In comparison, the ionic leakages at −6° C., −8° C. and −10° C. of NA and CA ACBP6-overexpressor (OE-3) plants were significantly lower (P<0.05) than wild type (FIG. 4B).

Figure 4C:
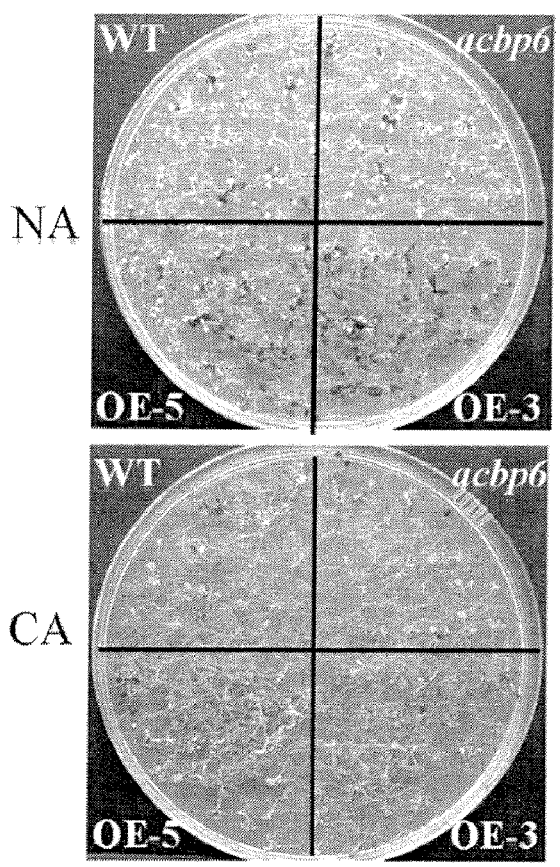
Figure 4D:
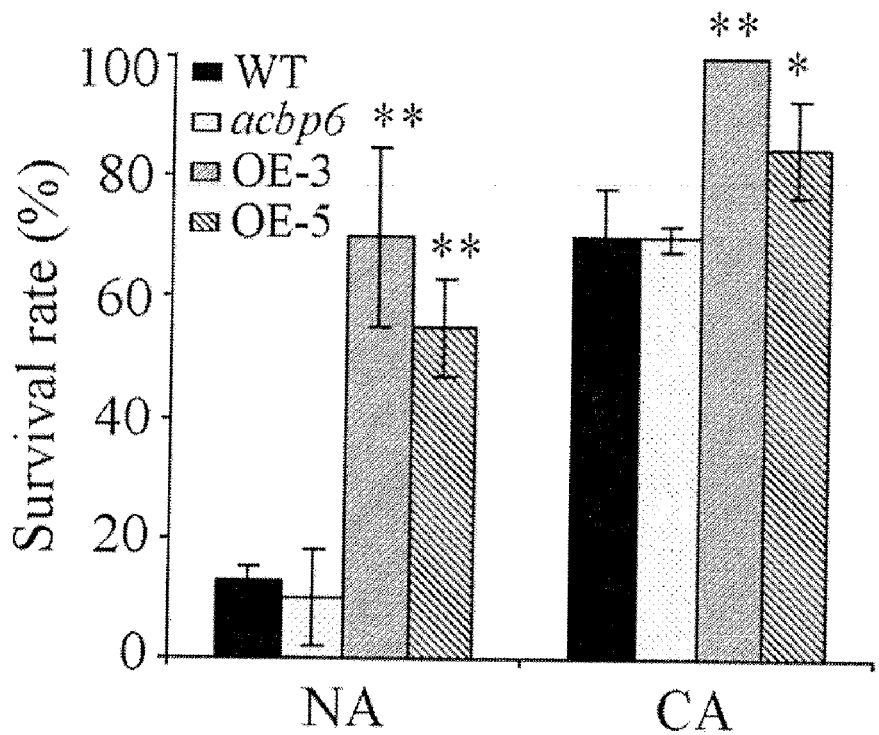

The effects of freezing treatment on seedling development were examined. NA and CA 11-day-old seedlings of wild type, acbp6 mutant and ACBP6-overexpressors (OE-3 and OE-5) were grown on MS medium and treated at −12° C. for 1 h. FIGS. 4C and 4D indicate that the survival rates for NA wild-type and NA acbp6 mutant seedlings were only 13% and 10%, respectively, significantly lower than those of ACBP6-overexpressing OE3 and OE5 (70% and 55%, respectively). With CA seedlings, 70% of wild-type and acbp6 mutant seedlings survived in comparison to 100% and 85% of ACBP6-overexpressors OE-3 and OE-5, respectively (FIGS. 4C and 4D). Results (average of 3 replicated experiments) were significant using the Student's t-test (P<0.01 or 0.05) and demonstrate that a knockout of ACBP6 expression resulted in enhanced sensitivity to freezing while the overexpression of ACBP6 in transgenic Arabidopsis conferred freezing tolerance.

When CA-treated flowers detached from 6-week-old wild type, acbp6 and ACBP6 OE-3 plants were subject to freezing treatment at −5° C. for 1 h, followed by a 7-day recovery at 4° C., the percentage of intact flowers remaining in the ACBP5 OE-3 lines was 70.6%, in comparison to 28.6% in wild type and 25.3% in the acbp6 mutant (FIGS. 12A-C).

Example 6

Figure 5A:
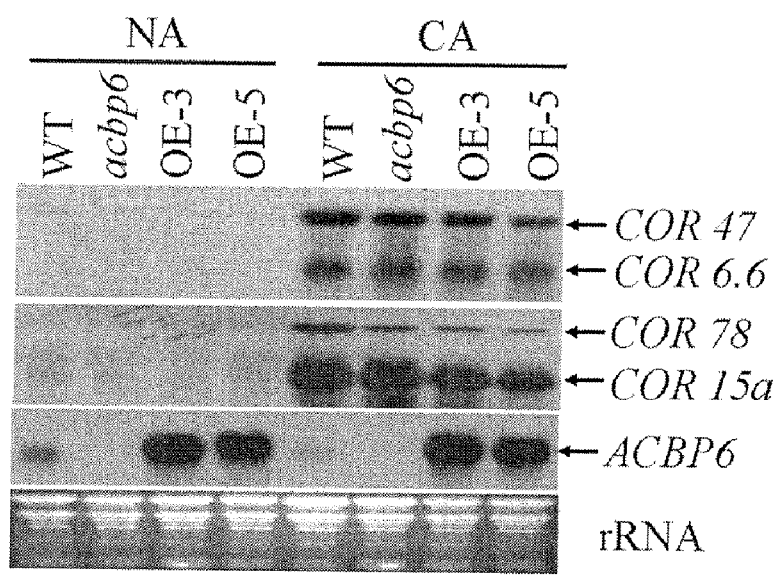

ACBP6-Associated Freezing Tolerance is not Dependent on Induced COR Gene Expression It has been observed that the expression of several cold-responsive (COR) genes are induced in many instances during CA (Thomashow, Plant Mol Biol 50: 571-599, 1999). The 4 major Arabidopsis COR genes (COR6.6, COR15a, COR47 and COR78) encode hydrophilic proteins that stabilize membranes during freezing-induced dehydration (Thomashow, Plant Mol Biol 50: 571-599, 1999). It has been shown that COR15a overexpression in transgenic Arabidopsis enhanced freezing tolerance in isolated protoplasts (Steponkus et al., Proc Natl Acad Sci USA 95: 14570-14575, 1998). To test whether ACBP6-conferred freezing tolerance is associated with induced COR gene expression, northern blot analyses were carried out to examine the expression of these 4 genes using PCR-generated probes. In NA wild type (Col-0), acbp6 mutant and ACBP6-overexpressors (OE-3 and OE-5), the COR6.6, COR15a, COR47 and COR78 transcripts were not detected. In contrast, these COR genes were induced after CA in all 3 genotypes (FIG. 5A). Although CA promotes ACBP6-conferred freezing tolerance, expression of these 4 COR genes were not further enhanced in OE-3 and OE-5 plants, indicating that ACBP6-conferred freezing tolerance is independent of induced COR gene expression.

Example 7

ACBP6-Conferred Freezing Tolerance is Related to Enhanced PLDδ Expression

Figure 5B:
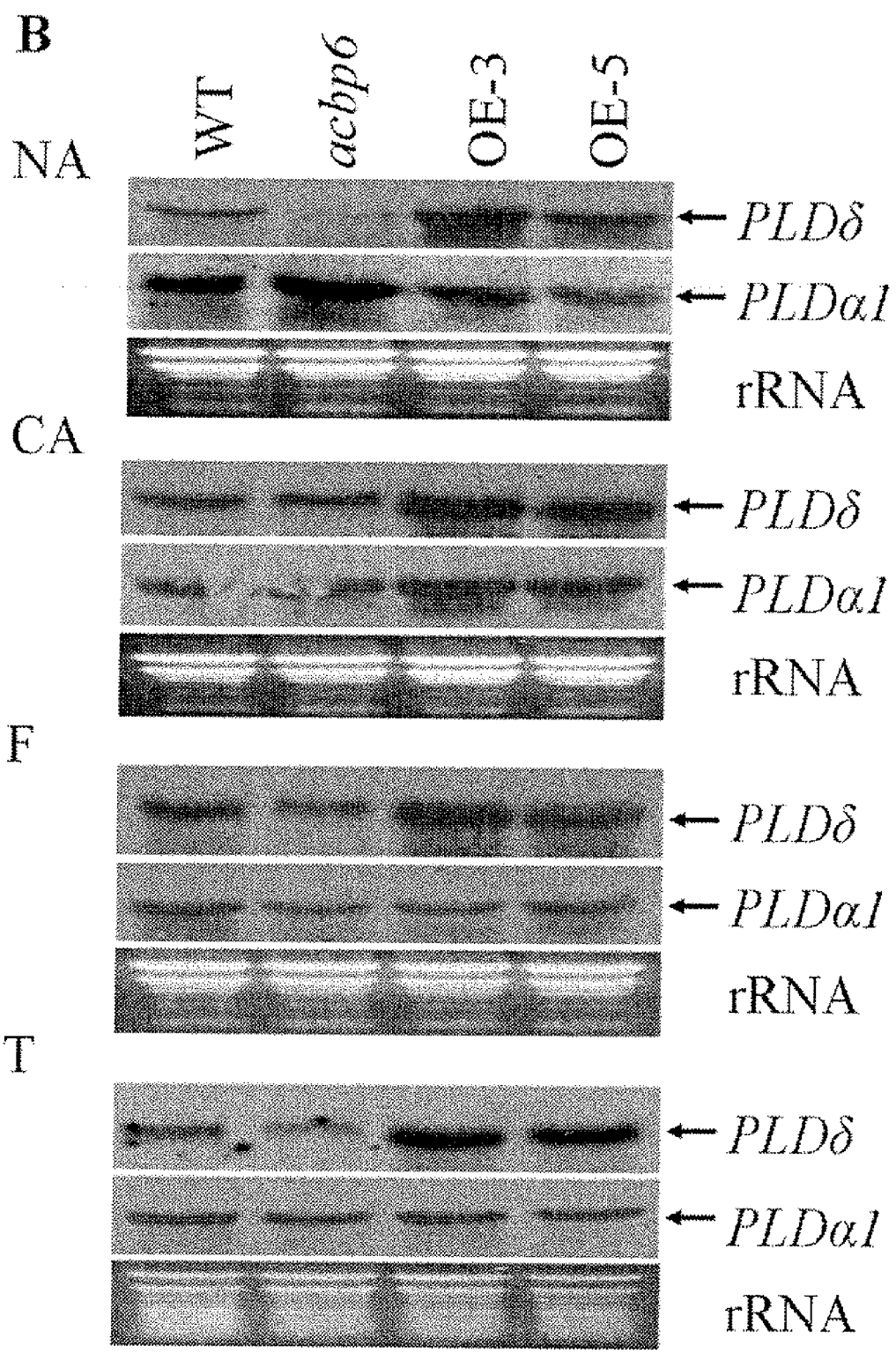

Two phospholipases, PLDα1 and PLDδ, are important in mediating freezing tolerance in Arabidopsis, (Welti et al., J Biol Chem 277: 31994-32002, 2002; Li et al., Nat Biotechnol 22: 427-433, 2004; Rajashekar et al., J Plant Physiol 163: 916-926, 2006; Li et al., J Biol Chem 283: 461-468, 2008) PLDα1-suppressed (Welti et al., J Biol Chem 277: 31994-32002, 2002; Rajashekar et al., J Plant Physiol 163: 916-926, 2006) and PLDδ-overexpressed (Li et al., 2004) Arabidopsis exhibit freezing tolerance. To investigate possible modulations in PLD expression in ACBP6-conferred freezing tolerance, the expression of PLDα1 and PLDδ in wild type, acbp6 mutant and ACBP6-overexpressors were examined by northern blot analyses using PCR-generated digoxygenin-labelled cDNA probes. Transcript levels of PLDδ were higher in ACBP6-overexpressors (OE-3 and OE-5) than wild type at NA, CA, freezing or thawing stages, while the acbp6 mutant showed lower expression than the OE lines (FIG. 5B). In comparison, PLDα1 expression in OE-3 and OE-5 lines was lower than wild type and the acbp6 mutant at NA stage but its expression in OE lines was higher than wild-type and mutant at CA stage (FIG. 5B).

Example 8

Changes in Lipid Molecular Species Following Freezing Treatment of CA Wild-Type and ACBP6-Overexpressor Plants No significant changes were observed in the lipid compositions between acbp6 mutant and wild type before and after CA followed by freezing treatment (Table 1). However, analyses of lipid compositions of wild type and ACBP6-overexpressors (OE-3 and OE-5), before and after CA followed by freezing treatment (−8° C.) displayed in FIG. 6 indicate several significant differences after treatment. Comparison of leaf samples from wild type and the ACBP6-overexpressors (OE-3 and OE-5) before treatment (grown at 23° C.) showed no significant differences in the total amounts of phosphatidic acid (PA), phosphatidylcholine (PC), digalactosyldiacylglycerol (DGDG), monogalactosyldiacylglycerol (MGDG), phosphatidylethanolamine (PE), phosphatidylglycerol (PG), phosphatidylinositol (PI), lysoPG, lysoPC and lysoPE, except for a slight decrease in phosphatidylserine (PS) content in the ACBP6-overexpressors (Table 2). However, following CA and freezing treatment, significant differences (P<0.05) were observed in the total amounts of PA and PC between wild type and both ACBP6-overexpressors OE-3 and OE-5 (Table 2). The total amount of PA in wild type increased 29-fold, while 49- and 57-fold increases occurred in OE-3 and OE-5, respectively (Table 2). Hence, the ACBP6-overexpressors accumulated 73% (OE-3) and 67% (OE-5) more PA than wild type. In particular, the 34:3 PA, 34:2 PA, 36:6 PA, 36:5 PA, 36:4 PA, 36:3 PA and 36:2 PA contents in the ACBP6 overexpressors were significantly higher than wild type (P<0.05) (FIG. 6A).

In contrast, the PC content decreased in both genotypes after CA followed by freezing. The total amount of PC decreased by 25% in wild type and 51% and 58% in the ACBP6-overexpressors OE-3 and OE-5, respectively. Further OE-3 and OE-5 accumulated 36% and 46% less PC, respectively, than wild type (P<0.05). In particular, the molecular species 32:0 PC, 34:4 PC, 34:3 PC, 34:2 PC, 36:6 PC, 36:5 PC, 36:4 PC, 36:3 PC, 36:2 PC, 38:6 PC, 38:5 PC, 38:4 PC, 38:3 PC, 38:2 PC, 40:5 PC and 40:4 PC in the ACBP6 overexpressors OE-3 and OE-5 were significantly lower (P<0.05) than wild type (FIG. 6B). Interestingly, the decreases in species of 34:3 PC, 34:2 PC, 36:6 PC, 36:5 PC, 36:4 PC, 36:3 PC and 36:2 PC (FIG. 6B, in boldface) corresponded well to increases in species of PA (FIG. 6A, number in boldface).

Example 9

$(His)_6$-ACBP6 Interacts with Phosphatidylcholine In Vitro

Figure 7B:
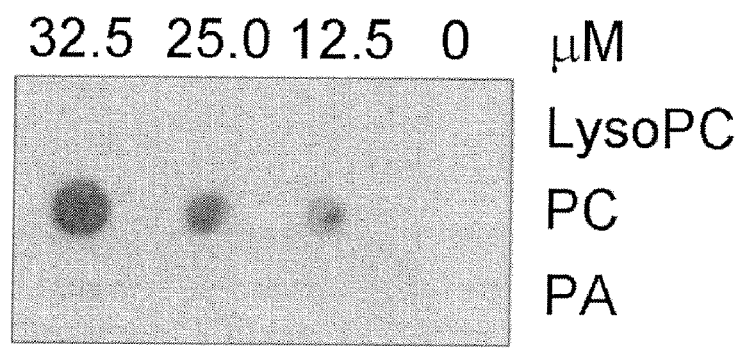
Figure 7C:
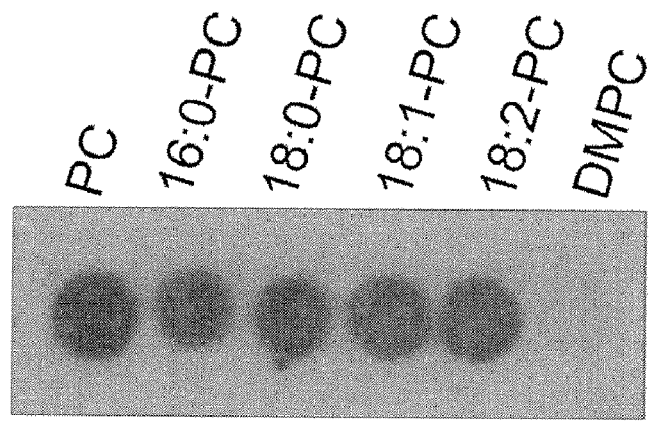

The 18.9-kD His-tagged ACBP6 recombinant protein was expressed and purified from *Esherichia coli* (FIG. 7A) for in vitro filter-binding assays to test the interactions between ACBP6 and various phospholipids PC, PA and LysoPC. Results from these assays indicated that $(His)_6$-ACBP6 binds PC, but not PA or LysoPC (FIG. 7B). As the PC used in FIG. 7B is 1,2-diacyl-sn-glocero-3-phosphocholine, which consists of 33% 16:0, 13% 18:0, 31% 18:1 and 15% 18:2 fatty acids, the binding of several fatty acid species of PC to $(His)_6$-ACBP6 was subsequently tested. Results showed that $(His)_6$-ACBP6 binds most species of PC (16:0-PC, 18:0-PC, 18:1-PC, 18:2-PC) tested, but did not bind 1,2-dimyristoyl-sn-glycero-3-phosphocholine (DMPC) (FIG. 7C).

Materials and Methods

Example 10

Plant Materials, Growth Conditions and Stress Treatments

For northern blot analysis, total RNA was extracted from rosettes of 4-week-old *A. thaliana* wild-type Columbia (ecotype Col-0) plants grown at 16 h light (23° C.)/8 h dark (21° C.) cycles. For 4° C. treatment, 4-week-old Col-0 plants were transferred from a plant growth chamber (16 h light (23° C.)/8 h dark (21° C.) cycles) to a 4° C. cold room under white light, and rosettes were harvested at 0, 6, 12, 24 and 48 h post-treatment.

The acbp6 allele is a T-DNA insertion mutant SALK_104339 from the SALK collection (http://signal.salk.edu/) obtained from TAIR (http://www.arabidopsis.org/). For growth on MS medium (Murashige and Skoog, Physiol Plant 15: 473-497, 1962) supplemented 2% sucrose, seeds of *A. thaliana* wild-type, acbp6 mutant and ACBP6-overexpressing transgenic *Arabidopsis* (ecotype Col-0) were surface-sterilized and chilled at 4° C. for 2 d. Subsequently, seeds were germinated and grown on MS medium supplemented with 2% sucrose under 16 h light (23° C.)/8 h dark (21° C.) cycles. Soil-grown plants were also grown under 16 h light (23° C.)/8 h dark (21° C.) cycles.

Freezing treatment was carried out following Zhu et al. (*Proc Natl Acad Sci USA* 101: 9873-9878, 2004). NA plants were grown in a growth chamber under 16 h light (23° C.)/8 h dark (21° C.) cycles until treatment while CA plants were transferred from the growth chamber to a cold room (4° C.) and grown for 3 days prior to treatment. Soil-grown plants (5-week-old) or 11-day-old seedlings grown in MS medium plates were subject to a temperature drop from 4° C. to −2° C. at 2° C. per h in the growth chamber (Watlow Series 942). When the temperature reached −2° C., ice crystals were placed on the plates or soil to induce crystallization and prevent super-cooling. After 2 h at −2° C., the temperature was lowered to −12° C. at 2° C. per h. After 1 h at the final temperature, the plants or seedlings were thawed at 4° C. overnight. Following recovery for 7 days under 16 h light (23° C.)/8 h dark (21° C.) cycles, the plants were photographed.

Example 11

Generation of 35S::ACBP6-GFP Transgenic Lines

To investigate the subcellular localization of ACBP6, an ACBP6-GFP fusion was prepared by Reverse Transcriptase-PCR of a 369-bp ACBP6 cDNA using RNA from wild-type *Arabidopsis* and ACBP6-specific primers ML750 (5'-ATAT GGATCCCACGCGTTGTCCTCGTCTTCT-3', BamHI site underlined) (SEQ. ID No: 8) and ML838 (5'-CA GGATCCTGAAGCCTTGGAAGCAGCAACT-3', BamHI site underlined) (SEQ. ID No: 9). The PCR product was digested with BamHI and cloned into the BamHI restriction site on plasmid pBI121-eGFP (Shi et al., *Plant Cell* 17: 2340-2354, 2005) to yield plasmid pAT376 in which ACBP6 was transcribed from the CaMV 35S promoter.

The plant transformation vector was mobilized from *E. coli* to *A. tumefaciens* strain LBA4404 by tri-parental mating (Horsch et al., Science 227: 1229-1231, 1985). The resultant *Agrobacterium* was used in plant transformation of *A. thaliana* wild type by the floral dip method (Clough and Bent, Plant J 16: 735-743, 1998). Putative transgenic plants expressing ACBP6-GFP, were selected on MS medium containing kanamycin (50 μg ml$^{-1}$) and verified by PCR using a CaMV 35S promoter-specific forward primer 35SB (5'-CAATCCCACTATCCTTCGCAAGACC-3') (SEQ. ID No: 10) and gene-specific reverse primer ML838, followed by northern blot analysis using an ACBP6 full-length cDNA and western blot analyses using ACBP6-specific antibodies and anti-GFP antibodies. Subsequently, the $T_2$ homozygous lines were tested on kanamycin-containing MS medium and the resistant plants were used in further analyses.

Example 12

Northern Blot Analysis

Rosettes from 4-week-old plants grown at 23° C. or 4° C. were collected in liquid nitrogen at the indicated times following treatment. Total RNA was extracted using TRIzol reagent (Invitrogen) following the manufacturer's protocol.

Northern blot analysis was carried out by using the Digoxigenin Nucleic Acid Detection Kit (Roche, Germany). Equal amounts of RNA (30 µg) were separated on a 1.5% agarose gel containing 6% formaldehyde and transferred to Hybond-N membranes (Amersham). The PCR Digoxigenin Probe Synthesis Kit was used to generate cDNA probes according to the manufacturer's instructions (Roche). The gene-specific primers used were ML750 and ML751 (5'-AATATATCATCTTGAATTCAACTG-3') (SEQ. ID No: 11) for ACBP6; ML880 (5'-GCTAACATGAGCTGTTCTCAC-3') (SEQ. ID No: 12) and ML881 (5'-GAATGTGACGGT-GACTGTGG-3') (SEQ. ID No: 13) for COR15a; ML882 (5'-CAGAGACCAACAAGAATGCC-3') (SEQ. ID No: 14) and ML883 (5'-CGTAGTACATCTAAAGGGAG-3') (SEQ. ID No: 15) for COR6.6; ML884 (5'-CAAGATTACTCT-GCTAGAGGAGC-3') (SEQ. ID No: 16) and ML885 (5'-GTATACGATGAGTGTTATGGG-3') (SEQ. ID No: 17) for COR47; ML886 (5'-CAGAGGAACCACCACTCAAC-3') (SEQ. ID No: 18) and ML887 (5'-CTCCTCTGTTTTCT-CATCTC-3') (SEQ. ID No: 19) for COR78, ML921 (5'-TAT-GCGACGATTGATCTGCA-3') (SEQ. ID No: 20) and ML922 (5'-CTGAGAGCCTGAATCACATC-3') (SEQ. ID No: 21) for PLDα1; and ML923 (5'-AGCGACTCTAGCTC-GAACAC-3') (SEQ. ID No: 22) and ML924 (5'-CAAGCAT-AAGAAGAACCCAG-3') (SEQ. ID No: 23) for PLDδ. Hybridization and detection were performed according to standard procedures as specified by the manufacturer (Roche).

Example 13

Western Blot Analysis

Total plant protein for western blot analysis was extracted from 4-week-old plants of wild-type *A. thaliana*, acbp6 mutant, ACBP6-overexpressors and 35S::ACBP6-GFP transgenic lines. Protein concentration was determined by the method of Bradford (*Anal Biochem* 72: 248-254, 1976). Fifteen µg of total protein was loaded per well in SDS-polyacrylamide gel electrophoresis. The proteins were electrophoretically transferred to Hybond-C membrane (Amersham) using the Trans-Blot cell (Bio-Rad). ACBP6-specific and anti-GFP antibodies (Invitrogen) were used in western blot analyses. To generate ACBP6-specific antibodies, a synthetic peptide (VEGKSSEEAMNDY) (SEQ. ID No: 24) corresponding to amino acids 63 to 75 of ACBP6 was used for immunization of rabbits.

For analyses of subcellular fractions of plant protein in western blots, protein was extracted from 3-week-old rosettes of 35S::ACBP6-GFP line 1 and wild-type (Col-0) *Arabidopsis* that had been confirmed by northern blot analysis and western blot analysis. Subcellular fractionation was carried out by differential centrifugation according to Smith et al. (Planta 174: 462-472, 1988).

Example 14

Laser-Scanning Confocal Microscopy

A Zeiss LSM 510 inverted confocal laser-scanning microscope equipped with helium/neon lasers and multitracking was used for the analysis of ACBP6-GFP localization. GFP fluorescence was excited at 488 nm, filtered through a primary dichroic (UV/488/543), a secondary dichroic of 545 nm and subsequently through BP505-530 nm emission filters to the photomultiplier tube (PMT) detector. The images were processed using the LSM 510 software (Zeiss, Jena, Germany).

Example 15

Identification of an acbp6 Mutant

The acbp6 T-DNA insertion mutant (SALK_104339) was screened from a T-DNA seed pool prepared by the SALK Institute Genomic Analysis Laboratory (http://signal.salk.edu/). The T-DNA insertion in the gene was identified by using T-DNA left border primer LBa1 (5'-TTTTTCGC-CCTTTGACGTTGGA-3') (SEQ. ID No: 25) and ACBP6-specific forward primer ML770 (5'-ACTGAT-CACGCTTTTTCTCTG-3') (SEQ. ID No: 26) and reverse primer ML771 (5'-TTCTGGTATAGCTCCTGCCTG-3') (SEQ. ID No: 27). The PCR product was sequenced and the T-DNA insertion site was confirmed. Individual homozygous T-DNA mutant plants were identified by PCR. PCR amplification was initiated with denaturation at 95° C. for 3 min, followed by 30 cycles of 94° C. for 30 s, 55° C. for 30 s and 72° C. for 1 min, and another extension at 72° C. for 10 min.

Example 16

Generation of ACBP6-Overexpressing Plants

A 0.6-kb full-length cDNA of ACBP6 was amplified by RT-PCR using RNA isolated from wild-type *Arabidopsis* plants and ACBP6-specific primer pair ML750 (SEQ. ID No: 8) and ML751 (5'-AATATATCATCTTGAATTCAACTG-3', EcoRI site underlined) (SEQ. ID No: 11), The PCR product was cloned into pGEM-T Easy vector (Promega) to generate pAT323. The ACBP6 SpeI-EcoRI fragment from pAT323 was inserted into similar restriction sites on binary vector pSMB (Mylne and Botella, Plant Mol Biol Rep 16: 257-262, 1998) to generate plasmid pAT332. In the resultant vector, expression of the ACBP6 cDNA is under the control of the CaMV 35S promoter.

The construct was mobilized from *E. coli* to *A. tumefaciens* strain LBA4404 by tri-parental mating (Horsch et al., Science 227: 1229-1231, 1985). The resultant *Agrobacterium* was used in plant transformation of *A. thaliana* Columbia (ecotype Col-0) by the floral dip method (Clough and Bent, Plant J 16: 735-743, 1998). The $T_1$ generation (designated ACBP6-OE) were selected using Basta (57.8 µg ml$^{-1}$ glufosinate solution) and were further verified by PCR using a CaMV 35S promoter-specific forward primer 35SB (SEQ. ID No: 10) and gene-specific reverse primer ML771 (SEQ. ID No: 27). The putative positive transformants were confirmed by northern blot analysis using an ACBP6 full-length cDNA probe and western blot analysis using ACBP6-specific antibodies.

Example 17

Electrolyte Leakage

Ionic leakage measurements were carried out according to Welti et al. (*J Biol Chem* 277: 31994-32002, 2002). Rosettes from NA and CA plants were collected 1 h after freezing at the indicated temperatures and then incubated at 4° C. for 24 h. Deionized water was added, and conductivity of the solution was measured after gentle agitation at 23° C. for 1 h. Total ionic strength was determined after heating the solution in a 100° C. water bath for 10 min and cooling to 23° C. Ionic leakage was determined using a conductivity meter (YSI Model 55).

Example 18

Lipid Profiling

Lipid extraction was carried out according to the protocol provided by the Kansas Lipidomics Research Center (www.K-state.edu/lipid/lipidomics). Five-week-old plants were CA for 3 d at 4° C. and then frozen at −8° C. for 2 h, following which rosettes from 2-3 plants were harvested immediately. The non-treated NA plants remained in a growth chamber at 23° C. until harvest. The rosettes were transferred immediately to 3 ml of isopropanol with 0.01% butylated hydroxytoluene at 75° C. and incubated for 15 min. Subsequently, 1.5 ml of chloroform and 0.6 ml of water were added. The tubes were shaken for 1 h, followed by removal of the extract for lipid analysis. The tissue was re-extracted with chloroform/methanol (2:1) with 0.01% butylated hydroxytoluene 4 to 5 times with 30 min agitation each, until all of the plant tissue turned white. The remaining plant tissue was heated overnight at 105° C. and weighed to yield "dry weight". The combined extracts were washed once with 1 ml of 1 M KCl and once with 2 ml of water, after which the solvent was evaporated under nitrogen. These samples were sent by courier service for lipid profiling at the Kansas Lipidomics Research Center.

Example 19

Purification of Recombinant His-Tagged ACBP6 for Filter-Binding Assays

Expression and purification of His-tagged ACBP6 recombinant protein was carried out according to Xiao et al. (*Plant J* 54: 141-151, 2008). Binding of $(His)_6$-ACBP6 to various lipids on filters was carried out as described previously (Zhang et al., *Proc Natl Acad Sci USA* 101: 9508-9513, 2004) with minor modifications. Briefly, various concentrations of lipids were spotted onto nitrocellulose and incubated at RT for 1 h in dark. LysoPC, PC, PA, 18:0-PC and 18:2-PC were purchased from Sigma, 16:0-PC, 18:1-PC and DMPC were purchased from Echelon Biosciences. The lipid-bound filter was blocked with TBS with 1% nonfat milk for 1 h. After incubated with 1 μg/ml of purified $(His)_6$-ACBP6 protein in blocking buffer for 2 h, the filter was gently washed 3 times with TTBS (TBS plus 0.1% Tween 20), each for 10 min. Following incubated with the HRP-conjugated anti-penta-His antibodies (1:2,000; QIAGEN, Cat. No. 1014922) for 1 h at RT, the filter was again washed 3 times with TTBS, each for 10 min and then detected with the ECL Western Blotting Detection Kit (Amersham) following the manufacturer's protocols.

Example 20

Sequences

Sequence data included herein can be found in the GenBank/EMBL data libraries under accession numbers NM_102916 (ACBP6), NM_129815 (COR15a), NM_121602 (COR6.6), NM_101894 (COR47), NM_124610 (COR78), NM_112443 (PLDα1), and NM_119745 (PLDδ).

Tables 1 and 2 and their related description in the text have been reproduced from Chen et at 2008; Plant Physiology 148: 304-315 (www.plantphysiol.org; copyright American Society of Plant Biologists)

TABLE 1

Total amount of lipid in each head group class in leaves of wild type (Col-0) and acbp6 mutant grown at 23° C. or CA followed by freezing at −8° C. Values are means ± SD (nmol/mg dry weight; n = 5). No significant differences between the wild type and mutant were observed.

| Lipid class | 23° C. | | −8° C. | |
| --- | --- | --- | --- | --- |
| | wild type | acbp6 | wild type | acbp6 |
| PC | 15.1 ± 2.0 | 15.7 ± 0.8 | 7.4 ± 1.2 | 6.5 ± 0.6 |
| PA | 0.21 ± 0.04 | 0.28 ± 0.07 | 9.2 ± 2.1 | 11.2 ± 1.06 |
| DGDG | 41.6 ± 6.9 | 42.7 ± 1.5 | 36.4 ± 2.7 | 33.8 ± 1.5 |
| MGDG | 160.4 ± 24.1 | 168.5 ± 9.0 | 128.7 ± 13.0 | 116.5 ± 7.8 |
| PG | 8.2 ± 1.3 | 8.8 ± 0.4 | 8.7 ± 0.6 | 8.2 ± 0.4 |
| PE | 9.9 ± 1.7 | 10.6 ± 0.7 | 4.9 ± 0.9 | 4.3 ± 0.3 |
| PI | 3.9 ± 0.7 | 4.0 ± 0.2 | 3.7 ± 0.1 | 3.7 ± 0.1 |
| PS | 0.9 ± 0.1 | 1.0 ± 0.1 | 0.5 ± 0.02 | 0.5 ± 0.02 |
| LysoPG | 0.01 ± 0.00 | 0.02 ± 0.00 | 0.05 ± 0.03 | 0.08 ± 0.01 |
| LysoPC | 0.03 ± 0.00 | 0.03 ± 0.00 | 0.18 ± 0.02 | 0.18 ± 0.03 |
| LysoPE | 0.05 ± 0.01 | 0.05 ± 0.00 | 0.07 ± 0.01 | 0.07 ± 0.00 |

TABLE 2

Total amount of lipid in each head group class in leaves of wild-type (Col-0) and ACBP6-overexpressing (OE-3 and OE-5) plants grown at 23° C. or CA followed by freezing at −8° C. Values are means ± SD (nmol/mg dry weight; n = 3). Significant differences (P < 0.05) from the wild type in the same experiment are indicated in boldface.

| Lipid class | 23° C. | | | −8° C. | | |
| --- | --- | --- | --- | --- | --- | --- |
| | wild type | OE-3 | OE-5 | wild type | OE-3 | OE-5 |
| PC | 15.1 ± 0.53 | 14.8 ± 0.54 | 14.7 ± 1.19 | 11.4 ± 0.80 | 7.3 ± 0.77[a] | 6.2 ± 0.51[a] |
| PA | 0.24 ± 0.02 | 0.25 ± 0.02 | 0.21 ± 0.03 | 7.06 ± 1.16 | 12.2 ± 0.4[b] | 11.9 ± 1.5[b] |
| DGDG | 40.1 ± 5.9 | 39.7 ± 1.5 | 38.4 ± 0.24 | 34.9 ± 2.5 | 35.1 ± 2.3 | 32.0 ± 1.2 |
| MGDG | 190.7 ± 29.2 | 179.0 ± 6.2 | 168.0 ± 4.7 | 113.1 ± 10.4 | 120.5 ± 10.0 | 97.3 ± 4.9 |
| PG | 8.2 ± 1.3 | 9.2 ± 0.4 | 8.1 ± 1.0 | 6.9 ± 0.8 | 6.8 ± 0.3 | 7.3 ± 1.6 |
| PE | 9.9 ± 1.7 | 11.6 ± 1.2 | 11.6 ± 2.1 | 4.9 ± 0.9 | 6.8 ± 1.5 | 6.4 ± 1.0 |
| PI | 4.5 ± 0.5 | 4.7 ± 0.2 | 4.4 ± 0.2 | 4.5 ± 0.2 | 4.5 ± 0.20 | 4.3 ± 0.3 |
| PS | 0.34 ± 0.03 | 0.25 ± 0.02[a] | 0.19 ± 0.00[a] | 0.13 ± 0.00 | 0.13 ± 0.02 | 0.13 ± 0.02 |
| LysoPG | 0.04 ± 0.01 | 0.04 ± 0.02 | 0.05 ± 0.06 | 0.13 ± 0.09 | 0.08 ± 0.04 | 0.08 ± 0.03 |
| LysoPC | 0.04 ± 0.00 | 0.05 ± 0.01 | 0.05 ± 0.01 | 0.38 ± 0.03 | 0.35 ± 0.03 | 0.30 ± 0.04 |
| LysoPE | 0.07 ± 0.00 | 0.09 ± 0.01 | 0.08 ± 0.01 | 0.25 ± 0.02 | 0.17 ± 0.01 | 0.12 ± 0.00 |

[a]Value is lower than wild type in the same experiment (P < 0.05).
[b]Value is higher than wild type in the same experiment (P < 0.05).

All patents, patent applications, provisional applications, and publications referred to or cited herein are incorporated by reference in their entirety, including all figures and tables, to the extent they are not inconsistent with the explicit teachings of this specification.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of obtaining enhanced low-temperature tolerance in a plant cell comprising:
   obtaining a plant cell genetically modified to express *Arabidopsis* acyl-CoA binding protein 6 (ACBP6) of SEQ ID NO:3, wherein the expression of ACBP6 conveys improved low-temperature tolerance when compared to a wild-type plant cell not genetically modified to express the ACBP6 of SEQ ID NO:3; and
   exposing the plant cell to temperatures low enough to be growth-inhibiting to a native plant cell of the same type.

2. The method of claim 1, wherein the plant cell is in a plant part.

3. The method of claim 2, wherein the plant part is in a plant.

4. The method of claim 2, wherein the plant part is a flower.

5. The method of claim 1, wherein the plant cell is of a solanaceous plant species.

6. The method of claim 5, wherein the plant cell is a tomato cell.

7. The method of claim 1, wherein the plant cell is of a grain crop.

8. The method of claim 7, wherein the plant cell is a rice cell.

9. The method of claim 1, wherein the plant cell is a cotton cell.

10. A method of obtaining a plant part having low-temperature tolerance, comprising:
    obtaining a plant part genetically modified to express *Arabidopsis* acyl-CoA binding protein 6 (ACBP6) of SEQ ID NO:3, wherein the expression of ACBP6 conveys improved low-temperature tolerance when compared to a wild-type plant part not genetically modified to express the ACBP6 of SEQ ID NO:3; and
    growing the plant part under conditions where it is exposed to frost or freeze.

11. The method of claim 10, wherein obtaining the plant part comprises growing the plant part from a seed.

12. The method of claim 10, wherein obtaining the plant part comprises obtaining a plant cutting.

13. The method of claim 10, wherein the plant part is in a plant.

14. The method of claim 10, wherein the plant part is a flower.

* * * * *

UNITED STATES PATENT AND TRADEMARK OFFICE
CERTIFICATE OF CORRECTION

PATENT NO. : 8,378,172 B2
APPLICATION NO. : 12/767177
DATED : February 19, 2013
INVENTOR(S) : Chye et al.

Page 1 of 1

It is certified that error appears in the above-identified patent and that said Letters Patent is hereby corrected as shown below:

In the Specification

Column 5,
Line 44, "16 h light [21°C.]/8 h dark [21°C.]" should read --16 h light [23 °C]/8 h dark [21 °C]--.

Column 7,
Line 65, "found in is "endogenous to")" should read --found in (e.g., is "endogenous to")--.

Column 14,
Lines 47-48, "N-nitrosourea (EN U)" should read --N-nitrosourea (ENU)--.

Column 18,
Line 48, "Eurosids H" should read --Eurosids II--.

Column 21,
Line 42, "(Gorlich and Mattaj" should read --(Görlich and Mattaj--.
Line 51, "Lack of this hand" should read --Lack of this band--.

Column 28,
Line 37, "(SEQ. ID No: 11), The" should read --(SEQ. ID No: 11). The--.

Column 30,
Line 36, "Chen et at 2008" should read --Chen et al 2008--.

Signed and Sealed this
Twenty-fourth Day of September, 2013

Teresa Stanek Rea
*Deputy Director of the United States Patent and Trademark Office*